United States Patent [19]
Garvey et al.

[11] Patent Number: 6,043,233
[45] Date of Patent: *Mar. 28, 2000

[54] COMPOSITIONS AND METHODS TO PREVENT TOXICITY INDUCED BY NONSTEROIDAL ANTIINFLAMMATORY DRUGS

[75] Inventors: David S. Garvey, Waltham; L. Gordon Letts, Dover; H. Burt Renfroe, Wellesley; Sang William Tam, Dover, all of Mass.

[73] Assignee: NitroMed, Inc., Bedford, Mass.

[ * ] Notice: This patent is subject to a terminal disclaimer.

[21] Appl. No.: 09/235,804

[22] Filed: Jan. 22, 1999

Related U.S. Application Data

[62] Division of application No. 08/931,564, Sep. 16, 1997, which is a continuation of application No. 08/543,208, Oct. 13, 1995, Pat. No. 5,703,073, which is a continuation-in-part of application No. 08/425,090, Apr. 19, 1995, abandoned.

[51] Int. Cl.$^7$ ............... A61K 31/192; A61K 31/407; A61K 31/603; A61K 31/606; A61K 31/60
[52] U.S. Cl. .................. 514/159; 514/19; 514/162; 514/165; 514/166; 514/413; 514/546; 514/567
[58] Field of Search ............... 514/19, 546, 413, 514/159, 162, 165, 166, 567

[56] References Cited

U.S. PATENT DOCUMENTS

| | | | |
|---|---|---|---|
| 4,556,672 | 12/1985 | Kadin | 514/414 |
| 5,621,000 | 4/1997 | Arena et al. | 514/411 |
| 5,700,947 | 12/1997 | Soldato | 548/491 |
| 5,703,073 | 12/1997 | Garvey et al. | 514/226.5 |
| 5,780,495 | 7/1998 | Del Soldato | 514/413 |

FOREIGN PATENT DOCUMENTS

| | | |
|---|---|---|
| WO 93/09806 | 5/1993 | WIPO. |
| 9404484 | 3/1994 | WIPO. |
| WO 94/12463 | 6/1994 | WIPO. |
| 9509831 | 4/1995 | WIPO. |
| 0658559 | 6/1995 | WIPO. |
| 9530641 | 11/1995 | WIPO. |
| 9716405 | 5/1997 | WIPO. |
| 9731654 | 9/1997 | WIPO. |
| 9809948 | 3/1998 | WIPO. |

OTHER PUBLICATIONS

Carty et al., *Agents Actions*, 39:157–165 (1993).
Conforti et al., *Agents Actions*, 40: 176–180 (1993).
Cuzzolin et al., *Pharmacol. Res.*, 29(1):89–97 (1994).
Goodman and Gilman's, *Pharmacological Basis for Therapeutics*, (8th Ed.):630–681 (1993).
Reuter et al., *Life Sci.*, 55(1):PL1–PL8 (1994).
Reuter et al., *Immunology, Microbiology and Inflam. Disorders*, A759 (1994).
Soll et al., *Annals of Internal Medicine*, 114:307–319 (1991).
Wallace et al., *Eur. J. Pharmacol.*, 257:249–255 (1994).
Wallace et al., *Gastroenterology*, 106(4):Part 2A208AGA Abstracts (1994).
Wallace et al., *Gastroenterol. and Hepatol.*, 9:S40–S44 (1994).
Wallace et al., *Novel Molecular Approaches to Anti–Inflammatory Theory*; Birkäuser Verlag, Basel:121–129 (1995).
Wallace et al., *Gastroenterology*, 107:173–179 (1994).

*Primary Examiner*—Richard L. Raymond
*Attorney, Agent, or Firm*—Hale and Dorr LLP

[57] ABSTRACT

Nonsteroidal antiinflammatory drugs which have been substituted with a nitrogen monoxide group; compositions comprising (i) a nonsteroidal antiinflammatory drug, which can optionally be substituted with a nitrogen monoxide group and (ii) a compound that directly donates, transfers or releases a nitrogen monoxide group (preferably as a charged species, particularly nitrosonium); and methods of treatment of inflammation, pain, gastrointestinal lesions and/or fever using the compositions are disclosed The compounds and compositions protect against the gastrointestinal, renal and other toxicities that are otherwise induced by nonsteroidal antiinflammatory drugs.

31 Claims, No Drawings

COMPOSITIONS AND METHODS TO PREVENT TOXICITY INDUCED BY NONSTEROIDAL ANTIINFLAMMATORY DRUGS

This application is a divisional of application Ser. No. 08/931,564, filed Sep. 16, 1997, which is a continuation of U.S. application Ser. No. 08/543,208, filed Oct. 13, 1995, issued as U.S. Pat. No. 5,703,073, which is a continuation-in-part of application Ser. No. 08/425,090, filed now Apr. 19, 1995 now abandoned.

This invention relates to the field of "aspirin-like" or nonsteroidal antiinflammatory drug compounds and compositions that prevent, reduce or reverse the gastrointestinal, renal, and other toxicities associated with nonsteroidal antiinflammatory drugs.

Arena et al., WO94/12463, discloses the chemistry and pharmacology of nitroxybutylester[$(CH2)_4$—$ONO_2$] derivatives of several aryl propionic acid non-steroidal antiinflammatory drugs including ketoprofen, flurbiprofen, suprofen, indobufen and etodolac. Studies on nitroxybutylester derivatives of flurbiprofen and ketoprofen are also reported in Wallace et al., *Gastroenterology*, 107:173–179 (1994). See, also, Cuzzolin et al., *Pharmcol. Res.*, 29(1):89–97 (1994); Reuter et al., *Life Sci.* (*USA*), 55/1(PL1–PL8) (1994); Reuter et al., *Gastroenterology*, 106(4):Suppl. A759 (1994); Wallace et al., *Eur. J. Pharmacol.*, 257(3):249–255 (1994); Wallace et al., *Gastroenterology*, 106(4):Suppl. A208 (1994); and Conforti et al., *Agents-Actions*, 40(3–4) :176–180 (1993). These publications uniformly examine and rely upon the use of indirectly linked nitrogen dioxide substitutions.

The present invention is based on the discovery by the inventors that it is possible to link a nitrogen monoxide group, nitric oxide (NO), to a non-steroidal antiinflammatory agent and that the resulting compounds not only possess potent analgesic/antiinflammatory properties but has a much reduced potential for producing gastrointestinal lesions (ulcers).

The present invention is further based on the discovery by the inventors that it is possible to coadminister a non-steroidal antiinflammatory drug (NSAID) and a compound that directly donates, releases or transfers nitrogen monoxide (preferably as a charged species, particularly nitrosonium) to prevent, reduce, or reverse the gastrointestinal, renal, and other toxicities induced by the NSAID. NSAIDs are antiinflammatory, analgesic and antipyretic compounds that act as cyclooxygenase, the enzyme responsible for the biosyntheses of the prostaglandins and certain autocoids, inhibitors, including inhibitors of the various isozymes of cyclooxygenase (including but not limited to cyclooxygenase-1 and -2) and as inhibitors of both cyclooxygenase and lipoxygenase. A nitric oxide donor is a compound that contains a nitric oxide moiety and which directly releases or directly chemically transfers nitrogen monoxide (nitric oxide), preferably in its positively charged nitrosonium form, to another molecule. Nitric oxide donors include but are not limited to S-nitrosothiols, nitrites, N-oxo-N-nitrosamines, and substrates of various forms of nitric oxide synthase.

In one aspect the present invention provides a compound comprising a non-steroidal antiinflammatory agent to which is directly or indirectly linked at least one NO group. The non-steroidal antiinflammatory agent can, for example, be an aryl propionic acid or an enolic anilide. The invention also provides compositions comprising such compounds in a pharmaceutically acceptable carrier.

In another aspect the invention provides a composition comprising a mixture of a therapeutically effective amount of a nonsteroidal antiinflammatory agent and an NSAID toxicity reducing amount of a compound that donates, transfers or releases nitric oxide.

In another aspect the present invention provides a composition comprising a non-steroidal antuinflammatory agent to which is directly or indirectly linked at least one NO group and a compound that donates, transfers or releases nitric oxide. The non-steroidal antdnflammatory agent can, for example, be an aryl propionic acid or an enolic anilide. The invention also provides compositions comprising such compounds in a pharmaceutically acceptable carrier.

In another aspect the invention provides a method for treating inflammation, pain and/or fever in an individual in need thereof which comprises administering to the individual a nonsteroidal antiinflammatory agent, which may optionally be substituted with at least one NO group, and a compound that donates, transfers or releases nitric oxide. The NSAID or NSAID directly or indirectly linked to at least one NO group, and nitric oxide donor can be administered separately or as components of the same composition.

In another aspect the invention provides a method of treating inflammation, pain and/or fever in an individual in need thereof which comprises administering to the individual a composition comprising a therapeutically effective amount of an NSAID, which may optionally be substituted with at least one NO group, and an NSAID toxicity reducing amount of a nitric oxide donor in a pharmaceutically acceptable carrier. Such compositions are discussed in more detail below.

In another aspect the invention provides a method to decrease or reverse the gastrointestinal toxicity of nonsteroidal antiinflammatory drugs administered to an animal, particularly a human, by co-administering to said animal a nitric oxide donor. The NSAID and nitric oxide donor can be administered separately or as components of the same composition.

In another aspect the invention provides a method to decrease or reverse the renal toxicity of nonsteroidal antiinflammatory drugs administered to an animal, particularly a human, by co-administering to said animal a nitric oxide donor. The NSAID and nitric oxide donor can be administered separately or as components of the same composition.

In another aspect the invention provides a method to accelerate gastrointestinal tissue repair in an animal, particularly a human, by administering to said animal a nitric oxide donor. The NSAID and nitric oxide donor can be administered separately or as components of the same composition.

The compounds and compositions of the present invention are novel and can be utilized to treat numerous inflammatory disease states and disorders. For example, reperfusion injury to an ischemic organ, e.g., reperfusion injury to the ischemic myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, disseminated intravascular coagulation, fatty embolism, Alzheimer's disease, adult and infantile respiratory diseases, carcinogenesis and hemorrhages in neonates.

The NSAID can be nitrosylated through sites such as oxygen (hydroxyl condensation), sulfur (sulfhydryl condensation), carbon and nitrogen.

The term "lower alkyl" herein refers to branched or straight chain alkyl groups comprising one to ten carbon atoms, including methyl, ethyl, propyl, isopropyl, n-butyl, t-butyl, neopentyl and the like.

The term "alkoxy" herein refers to RO-wherein R is lower alkyl as defined above. Representative examples of alkoxy groups include methoxy, ethoxy, t-butoxy and the like.

The term "alkoxyalkyl" herein refers to an alkoxy group as previously defined appended to an alkyl group as previously defined. Examples of alkoxyalkyl include, but are not limited to, methoxymethyl, methoxyethyl, isopropoxymethyl and the like.

The term "alkenyl" herein refers to a branched or straight chain $C_2$–$C_{10}$ hydrocarbon which also comprises one or more carbon-carbon double bonds.

The term "amino" herein refers to —$NH_2$.

The term "cyano" herein refers to —CN.

The term "hydroxy" herein refers to —OH.

The term "alkylsulfinyl" herein refers to $R_{50}$—S(O)$_2$— wherein $R_{50}$ is a branched or unbranched lower alkyl of up to four carbons.

The term "carboxamido" herein refers to —C(O)$NH_2$.

The term "carbamoyl" herein refers to —O—C(O)$NH_2$.

The term "carboxyl" herein refers to —$CO_2H$.

The term "alkylamino" herein refers to $R_{51}$NH— wherein $R_{51}$ is a lower alkyl group, for example, methylamino, ethylamino, butylamino, and the like.

The term "dialkylamino" herein refers to $R_{52}R_{53}$N— wherein $R_{52}$ and $R_{53}$ are independently selected from lower alkyl, for example dimethylamino, diethylamino, methyl propylamino, and the like.

The term "N-alkylcarbamoyl" herein refers to —O—C(O)N($R_{51}$)(H) wherein $R_{51}$ is as previously defined.

The term "N,N-dialkylcarbamoyl" herein refers to —O—C(O)N($R_{52}$)($R_{53}$) wherein $R_{52}$ and $R_{53}$ are as previously defined.

The term "nitroso" herein refers to the group —NO and "nitrosylated" refers to compounds that have been substituted therewith.

The term "aryl" herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from loweralkyl, haloalkyl, alkoxy, amino, alkylamino, dialkylamino, hydroxy, halo, and nitro. In addition, substituted aryl groups include tetrafluorophenyl and pentafluorophenyl.

The term "arylalkyl" herein refers to a lower alkyl radical to which is appended an aryl group. Representative arylalkyl groups include benzyl, phenylethyl, hydroxybenzyl, fluorobenzyl, fluorophenylethyl and the like.

The term "arylthio" herein refers to $R_{54}$S— wherein $R_{54}$ is an aryl group.

The term "cycloalkyl" herein refers to an alicyclic group comprising from 3 to 7 carbon atoms including, but not limited to, cyclopropyl, cyclobutyl, cyclopentyl, cyclohexyl and the like.

The term "bridged cycloalkyl" herein refers to two or more cycloalkyl radicals fused via adjacent or non-adjacent carbon atoms, including but not limited to adamantyl and decahydronapthyl.

The terms "halogen" or "halo" herein refer to I, Br, Cl or F. The term "haloalkyl" herein refers to a lower alkyl radical, as defined above, bearing at least one halogen substituent, for example, chloromethyl, fluoroethyl or trifluoromethyl and the like.

The term "heteroaryl" herein refers to a mono- or bi-cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two, or three substituents independently selected from lower alkyl, haloalkyl, alkoxy, amino, alkylamino, dialkylamino, hydroxy, halo and nitro. Examples of heteroaryl groups include but are not limited to pyridine, pyrazine, pyrimidine, pyridazine, pyrazole, triazole, thiazole, isothiazole, benzothiazole, benzoxazole, thiadiazole, oxazole, pyrrole, imidazole, and isoxazole.

The term "heterocyclic ring" herein refers to any 3-, 4-, 5-, 6-, or 7-membered nonaromatic ring containing at least one nitrogen atom which is bonded to an atom which is not part of the heterocyclic ring. In addition, the heterocyclic ring may also contain a one additional heteroatom which may be nitrogen, oxygen, or sulfur.

The term "heterocyclic compounds" herein refers to mono and polycyclic compounds containing at least one heteroaryl or heterocyclic ring.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof The NSAID used in the compositions of the invention can be any of those known to the art, including those exemplified below.

First, despite the introduction of many new drugs, aspirin (acetylsalicylic acid) is still the most widely prescribed antiinflammatory, analgesic and antipyretic agent and is a standard for the comparison and evaluation of all other NSAIDs. Salicylic acid itself is so irritating that it can only be used externally. However, derivatives, particularly salicylate esters and salts, have been prepared which provide ingestible forms of the salicylates which have the desired antiinflammatory and other properties. In addition to aspirin which is the acetate ester of salicylic acid, are the diflurophenyl derivative (diflunisal) and salicylsalicylic acid (salsalate). Also available are the salts of salicylic acid, principally sodium salicylate. Sodium salicylate and aspirin are the two most commonly used preparations for systemic treatment. Other salicylates include salicylamide, sodium thiosalicylate, choline salicylate and magnesium salicylate. Also available are combinations of choline and magnesium salicylates. Also contemplated are 5-aminosalicylic acid (mesalamine), salicylazosulfapyridine (sulfasalazine) and methylsalicylate.

Another group of NSAID drugs included are the pyrazolon derivatives. Included in this group are, for example, phenylbutazone, oxyphenbutazone, antipyrine, aminopyrine, dipyrone and apazone (azapropazone).

Another group of such NSAIDs are the para-aminophenol derivatives. These are the so-called "coal tar" analgesics and include phenacetin and its active metabolite acetaminophen.

Another group of compounds contemplated include indomethacin, a methylated indole derivative, and the structurally related compound, sulindac.

Also contemplated is a group of compounds referred to as the fenamates which are derivatives of N-phenylanthranilic acid. The most well known of these compounds are mefenamic, meclofenamic, flufenamic, tolfenamic and etofenamic acids. They are used either as the acid or as pharmaceutically acceptable salts.

Another contemplated NSAID is tolmetin which, like the other NSAIDs discussed herein, causes gastric erosion and prolonged bleeding time.

Another group of NSAID compounds are the propionic acid derivatives. Principal members of this group are ibuprofen, naproxen, flurbiprofen, fenoprofen and ketoprofen. Other members of this group, in use or study in countries outside the U.S., include fenbufen, pirprofen, oxaprozin, indoprofen and tiaprofenic acid.

Also contemplated are piroxicam and amperoxicam, oxicam derivatives which are a class of antiinflammatory enolic acids. The other related compounds tenoxicam and tenidap are also contemplated. Another compound that is particularly contemplated is diclophenac, one of the series of phenylacetic acid derivatives that have been developed as antiinflammatory agents. Other NSAIDs which are contemplated as suitable in the compositions of the invention include etodolac and nabumentone.

Each of the above contemplated NSAIDs is described more fully in the literature, such as in Goodman and Gilman, The Pharmacological Basis of Therapeutics (8th Edition), McGraw-Hill, 1993, Pgs. 638–381.

The compositions of the invention can also include NSAIDs which have been nitrosylated through sites such as oxygen (hydroxyl condensation), sulfur (sulfhydryl condensation), carbon and nitrogen, including those specifically discussed below and in the working examples that follow.

One embodiment of this aspect includes nitroso substituted compounds of the formula:

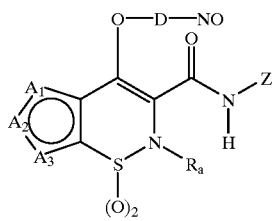

I wherein

D is selected from (i) a covalent bond; (ii) —C(R$_a$)— O—C(O)—Y—[C(R$_b$)(R$_c$)]$_p$—T— in which R$_a$ is lower alkyl, cycloalkyl, aryl or heteroaryl, Y is oxygen, sulfur, or NR$_i$ in which R$_i$ is hydrogen or lower alkyl, R$_b$ and R$_c$ are independently selected from, hydrogen, lower alkyl, cycloalkyl, aryl, heteroaryl, arylalkyl, alkylamino, dialkylamino or taken together are cycloalkyl or bridged cycloalkyl, p is an integer from 1 to 6 and T is a covalent bond, oxygen, sulfur, or nitrogen; or (iii) —(CO)—T$_1$—[C(R$_b$)(R$_c$)]$_p$—T$_2$— wherein T$_1$ and T$_2$ are independently selected from T, and wherein R$_b$, R$_c$, p and T are as defined above;

Z is an aryl or heteroaryl; and

A$_1$, A$_2$ and A$_3$ comprise the other subunits of a 5- or 6-membered monocyclic aromatic ring and each is independently selected from (1) C—R$_1$ wherein R$_1$ at each occurrence is independently selected from hydrogen, lower alkyl, lower haloalkyl, alkoxyalkyl, halogen or nitro; (2) N—R$_d$ wherein R$_d$ at each occurrence is independently selected from a covalent bond to an adjacent ring atom in order to render the ring aromatic, hydrogen, lower alkyl, cycloalkyl, arylalkyl, aryl, heteroaryl; (3) sulfur; (4) oxygen; and (5) B$_a$=B$_b$ wherein B$_a$ and B$_b$ are each independently selected from nitrogen or C—R$_1$ wherein at each occurrence R$_1$ is as defined above.

Another embodiment of this aspect is nitroso substituted compounds of the formula:

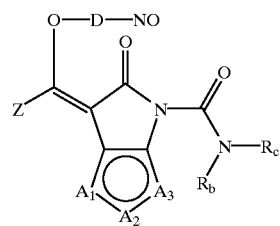

II wherein

R$_b$, R$_c$, D, Z, A$_1$, A$_2$ and A$_3$ are defined as above.

Another embodiment is compounds of the formula:

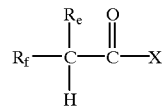

III wherein

R$_e$ is hydrogen or lower alkyl;

R$_f$ is selected from

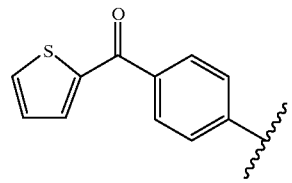

(1)

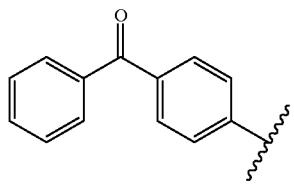

(2)

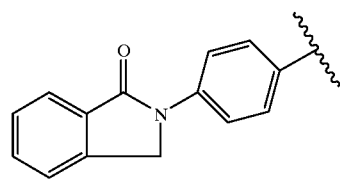

(3)

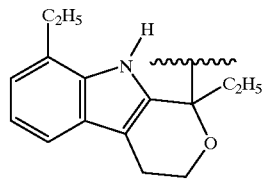

(4)

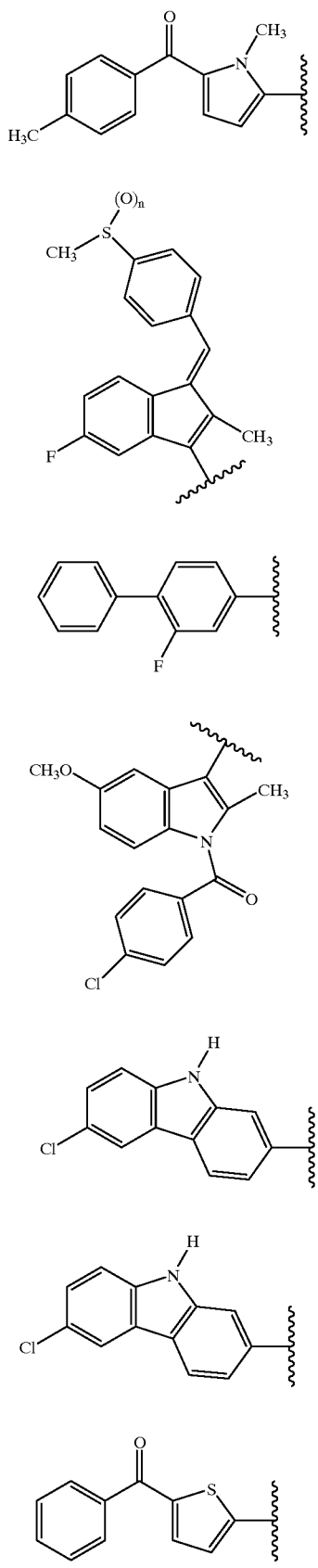
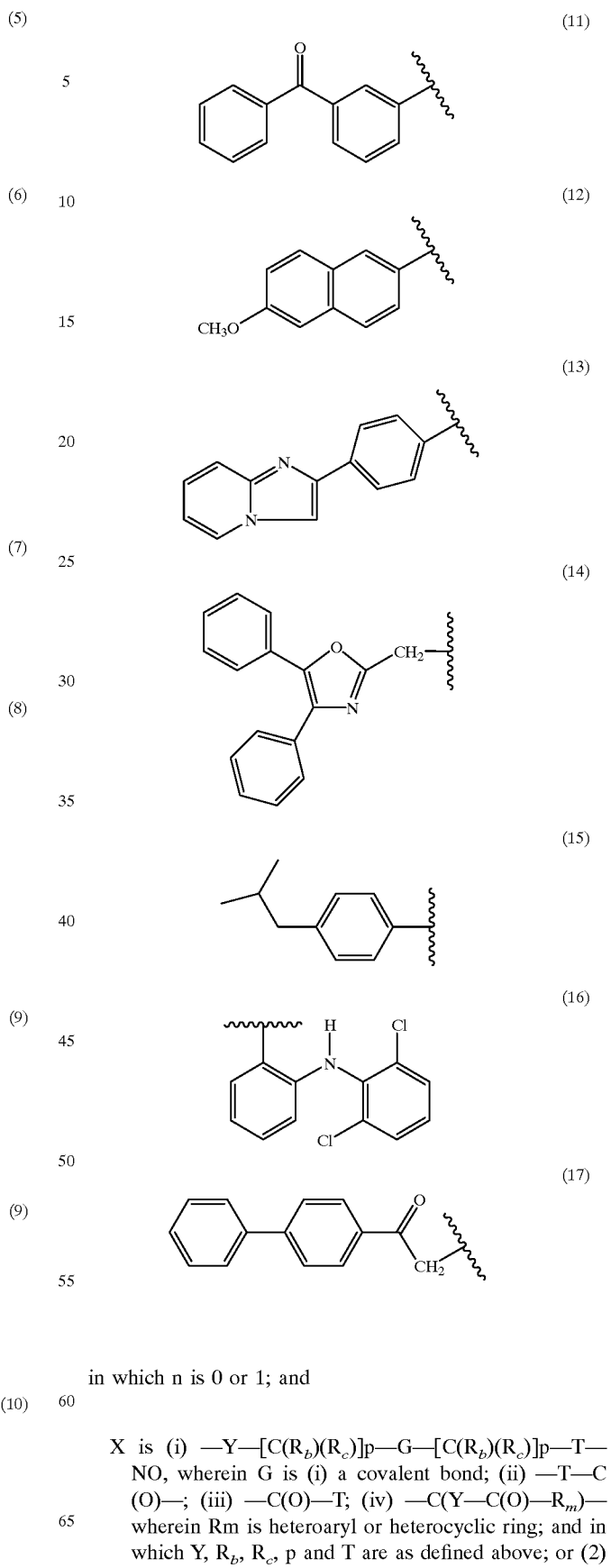
in which n is 0 or 1; and
X is (i) —Y—[C($R_b$)($R_c$)]p—G—[C($R_b$)($R_c$)]p—T—NO, wherein G is (i) a covalent bond; (ii) —T—C(O)—; (iii) —C(O)—T; (iv) —C(Y—C(O)—$R_m$)— wherein Rm is heteroaryl or heterocyclic ring; and in which Y, $R_b$, $R_c$, p and T are as defined above; or (2)

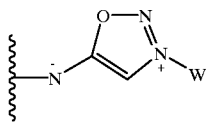

in which W is a heterocyclic ring or $NR_hR_i$ wherein $R_h$ and $R_i$ are independently selected from lower alkyl, aryl or alkenyl.

Another embodiment of this aspect is compounds of the formula:

IV

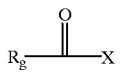

wherein $R_g$ is selected from (1)

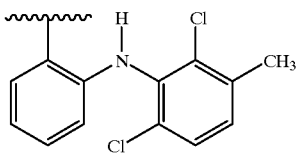

(2)

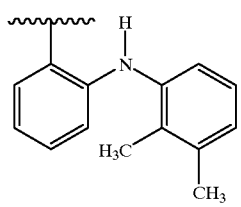

(3)

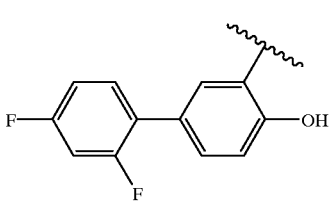

(4)

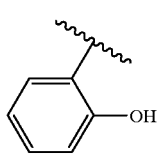

(5)

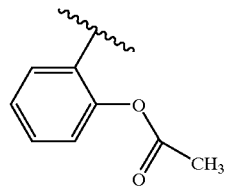

(6)

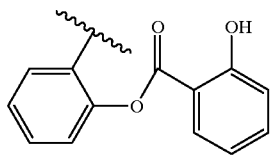

(7)

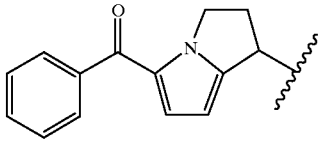

and X is defined as above.

The present invention also relates to processes for preparing the compounds of formula (I), (II), (III) or (IV) and to the intermediates useful in such processes.

Compounds of the present invention may be synthesized as shown in reaction Schemes I through XI presented below, in which $R_a$, $R_b$, $R_c$, $R_d$, $R_e$, $R_f$, $R_g$, $A_1$, $A_2$, $A_3$, p, and Z are as defined above or as depicted in the reaction schemes for formulas I, II, III or IV; $P^1$ is an oxygen protecting group and $P^2$ is a sulfur protecting group. The reactions are performed in solvents appropriate to the reagents and materials employed are suitable for the transformations being effected. It is understood by those skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur and oxygen protecting groups is well known in the art for protecting thiol, alcohol, and amino groups against undesirable reactions during a synthetic procedure and many such protecting groups are known, c.f., T. H. Greene and P. G. M. Wuts, *Protective Groups in Organic Synthesis*, John Wiley & Sons, New York (1991).

Nitroso compounds of formula (I) wherein $A_1$, $A_2$, $A_3$, $R_a$, and Z are defined as above and an O-nitrosyated enol is represenatative of the D group as defined above may be prepared according to reaction Scheme I. The enolic form of the β-keto amide of the formula 1 is reacted with a suitable nitrosylating agent such as thionyl chloride nitrite, thionyl dinitrite [c.f., Hakimelahi et al., *Helvetica Chimrica Acta*, 67, 907 (1984)], or nitrosium tetrafluoroborate in a suitable anhydrous solvent such as methylene chloride, tetrahydrofuran (THF), dimethylforamide (DMF), or acetonitrile with or without am amine base such as pyridine or triethylamine to afford the O-nitrite IA.

Scheme I

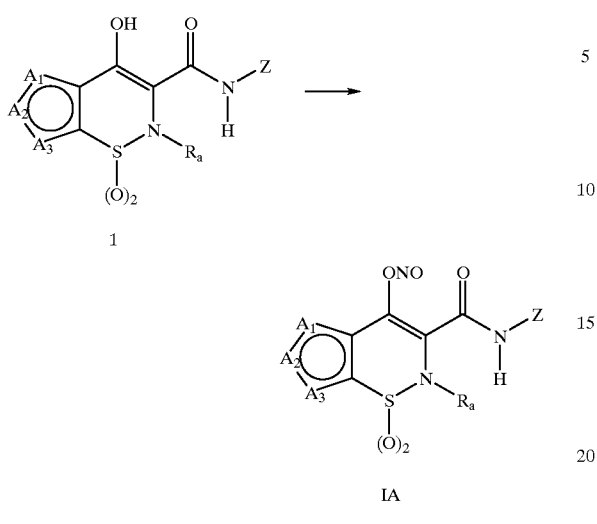

IA

Nitroso compounds of formula (I) wherein p, $A_1$, $A_2$, $A_3$, $R_a$, $R_b$, $R_c$, and Z are defined as above and an O-nitrosylated ester is representative of the D group as defined above may be prepared according to Scheme II. The enolic form of the b-keto amide of the formula 1 is converted to the ester of the formula 2 wherein p, $R_b$ and $R_c$ are defined as above by reaction with an appropriate protected alcohol containing activated acylating agent wherein $P_1$ is as defined above. Preferred methods for the formation of enol ester are reacting the enol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IB.

Scheme II

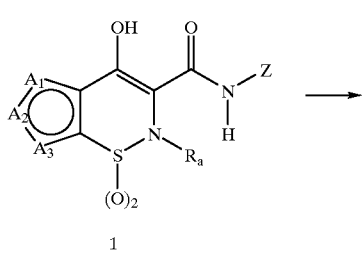

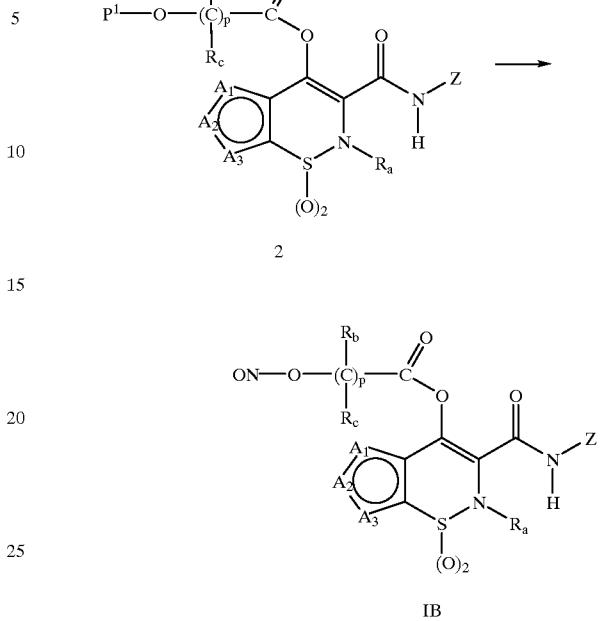

IB

Nitroso compounds of formula (I) wherein p, $A_1$, $A_2$, $A_3$, $R_a$, $R_b$, $R_c$, and Z are defined as above and an S-nitrosyated enol ester is representative of the D group as defined above may be prepared according to reaction Scheme III. The enolic form of the b-keto amide of the formula 1 is converted to the ester of the formula 3 wherein p, $R_b$, and $R_c$ are defined as above by reaction with an appropriate protected thiol containing activated acylating agent wherein $P^2$ is as defined above. Preferred methods for the formation of enol ester are reacting the enol with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as metheyene chloride, THF, DMF, or acetonitrile with or without an amine base such as pyridine or triethylamine affords the compound of the formula IC. Alternatively, reacting this intermediate with a stoichiometric quantity of sodium nitrite in aqueous acid affords the compound of the formula IC.

Scheme III

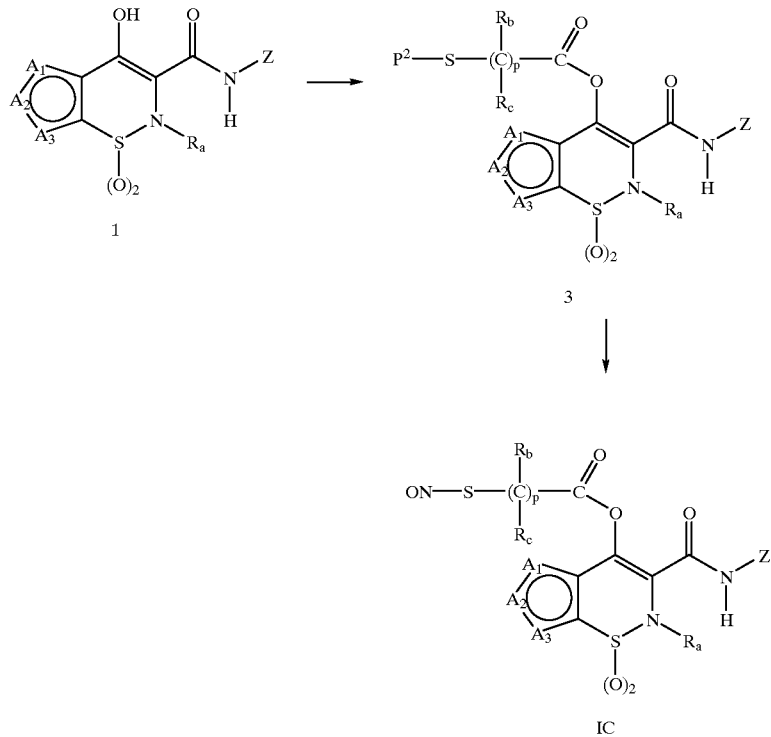

Nitroso compounds of formula (II) wherein p, $A_1, A_2, A_3$, $R_b$ and $R_c$, and Z are defined as above and an O-nitrosylated ester is representative of the D group as defined above may be prepared according to Scheme IV. The enolic form of the β-keto amide of the formula 4 is converted to the ester of the formula 5 wherein p, $R_b$ and $R_c$ are defined as above by reaction with an appropriate protected alcohol containing activated acylating agent wherein $P^1$ is as defined above. Preferred methods for the formation of enol ester are reacting the enol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IIA.

Scheme IV

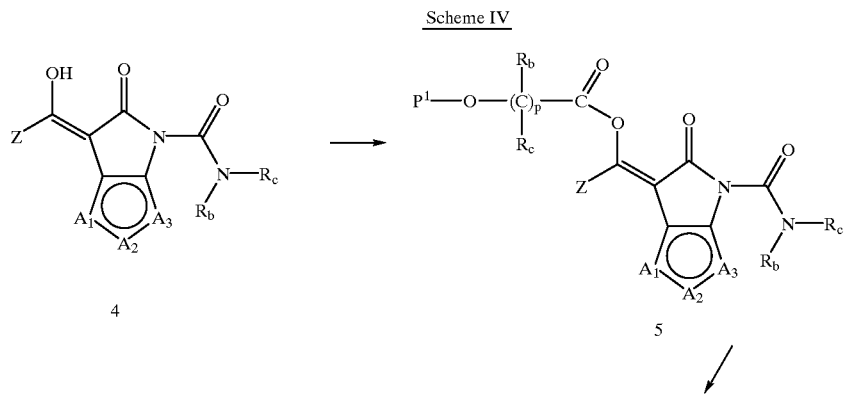

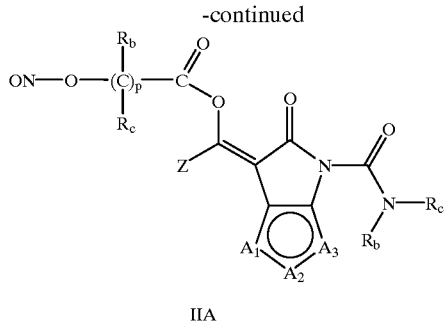

IIA

Nitroso compounds of formula (I) wherein p, $A_1$, $A_2$, $A_3$, $R_b$, $R_c$, and Z are defined as above and an S-nitrosyated enol ester is represenatative of the D group as defined above may be prepared according to reaction Scheme V. The enolic form of the β-keto amide of the formula 4 is converted to the ester of the formula 6 wherein p, $R_b$ and $R_c$ are defined as above by reaction with an appropriate protected thiol containing activated acylating agent wherein $P^2$ is as defined above. Preferred methods for the formation of enol ester are reacting the enol with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thiolesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine acid affords the compound of the formula IIB. Alternatively, reacting this intermediate with a stiochiometric quantity of sodium nitrite in aqueous acid affords the compound of the formula IIB.

Scheme V

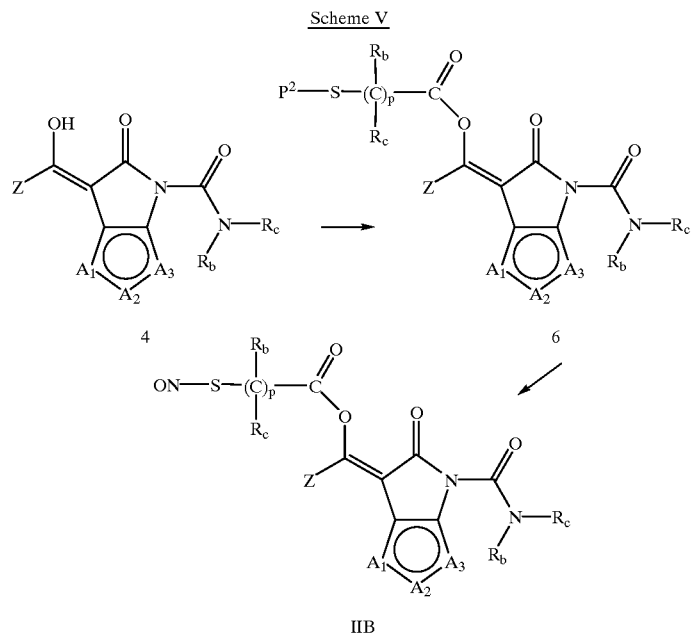

IIB

Nitroso compounds of formula (III) wherein p, $R_b$, $R_c$, $R_e$ and $R_f$ are defined as above and an O-nitrosylated ester is representative of the X group as defined above may be prepared according to Scheme VI. An acid of the formula 7 is converted into the ester of the formula 8 wherein p, $R_b$ and $R_c$ are defined as above by reaction with an appropriate monoprotected diol. Preferred methods for the preparation of esters are initially forming the mixed anhydride via reaction of 7 with a choroformate such as isobutylchloroformate in the presence of a non nucleophilic base such as triethylamine in an anhydrous inert solvent such as dichloromethane, diethylether, or THF. The mixed anhydride is then reacted with the monoprotected alcohol preferably in the presence of a condensation catalyst such as 4-dimethylamine pyridine. Alternatively, the acid 7 may be first converted to the acid chloride by treatment with oxalyl chloride in the presence of a catalytic amount of DMF. The acid chloride is then reacted with the monoprotected alcohol preferably in the presence of a condensation catalyst such as 4-dimethylamine pyridine and a tertiary amine base such as triethyl amine to afford the ester 8. Alternatively, the acid 7 and monoprotected diol may be coupled to afford 8 by treatment with a dehydration agent such as DCC. Alternatively, compound 7 may be first converted into an alkali metal salt such as the sodium, potassium, or lithium salt, and reacted with an alkyl halide which also contains a protected hydroxyl group in an polar solvent such as DMF to afford 8. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IIIA.

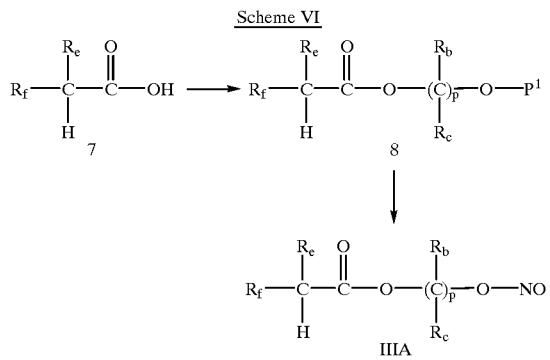

Nitroso compounds of formula (III) wherein p, $R_b$, $R_c$, $R_e$, and $R_f$ are defined as above and a S-nitrosylated ester is representative of the X group as defined above may be prepared according to Scheme VII. An acid of the formula 7 is converted into the ester of the formula 9 by reaction with an appropriate protected thiol containing alcohol. Preferred methods for the preparation of esters are initially forming the mixed anhydride via reaction of 7 with a chloroformate such as isobutylchloroformate in the presence of a non nucleophilic base such as triethylamine in an anhydrous inert solvent such as diethylether or THF. The mixed anhydride is then reacted with the thiol containing alcohol preferably in the presence of a condensation catalyst such as 4-dimethylamine pyridine. Alternatively, the acid 7 may be first converted to the acid chloride by treatment with oxalyl chloride in the presence of a catalytic amount of DMF. The acid chloride is then reacted with the monoprotected thiol preferably in the presence of a condensation catalyst such as 4-dimethylamine pyridine and a tertiary amine base such as triethyl amine to afford the ester 9. Alternatively, the acid and thiol containing alcohol may be coupled to afford 9 by treatment with a dehydration agent such as DCC. Alternatively, compound 7 may be first converted into an alkali metal salt such as the sodium, potassium, or lithium salt, and reacted with an alkyl halide which also contains a protected thiol group in an polar solvent such as DMF to afford 9. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thiolesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of the formula IIIB. Alternatively, this intermediate may be reacted with a stoichiometric quantity of sodium nitrite in aqueous acid affords the compound of the formula IIIB.

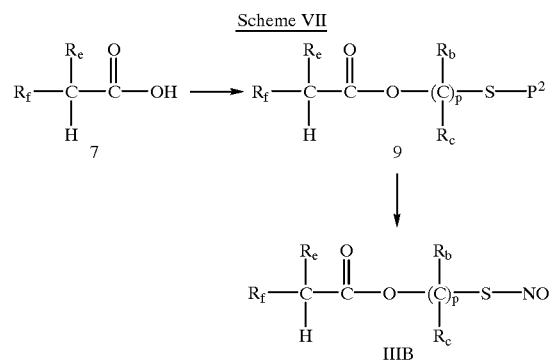

Nitroso compounds of formula (m) wherein W, $R_e$, and $R_f$ are defined as above and a 6-W-substituted sydnonimine wherein W is as defined above is representative of the X group as defined above may be prepared according to Scheme VIII. An acid of the formula 7 is converted into the carboximide of the formula IIIC by reaction with a 6-W-substituted sydnonimine. Preferred methods for the preparation of carboximides are initially forming the mixed anhydride via reaction of 7 with a chloroformate such as isobutylchloroformate in the presence of a non nucleophilic base such as triethylamine in an anhydrous inert solvent such as diethylether or THF. The mixed anhydride is then reacted with the 6-W-substituted sydnonimine to afford IIIC. Alternatively, the acid 7 may be coupled to the 6-W-substituted sydnonimine to afford IIIC by treatment with a dehydration agent such as DCC. Alternatively, the acid 7 may be converted into an active ester by reaction with a suitably substituted phenol utilizing any of the conditions for ester formation described for Scheme VI, followed by reaction with a 6-W-substituted sydnonimine. Preferred 6-W-substituted sydnonimines are 1,2,6,4-oxatriazolium, 6-amino-6-morpholine and 1,2,6,4-oxatriazolium, 6-amino-6-(6-chloro-2-methyl -benzene) and preferred active esters are para-nitrophenyl, 2,4,5-trichlorophenyl, and pentafluorophenyl.

Scheme VIII

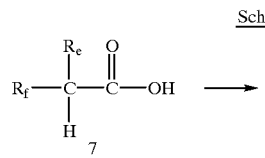

-continued

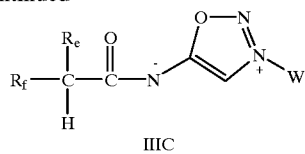

IIIC

Nitroso compounds of formula (IV) wherein p, $R_b$, $R_c$, and $R_g$ are defined as above and an O-nitrosylated ester is representative of the X group as defined above may be prepared according to Scheme IX. An acid of the formula 10 is converted into the ester of the formula 11 wherein p, $R_b$, and $R_c$ are defined as above, by reaction with an appropriate monoprotected diol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether or THF. The mixed anhydride is then reacted with the monoprotected alcohol preferably in the presence of a condensation catalyst such as 4-dimethylamine pyridine. Alternatively, the acid 10 may be first converted to the acid chloride by treatment with oxalyl chloride in the presence of a catalytic amount of DMF. The acid chloride is then reacted with the monoprotected alcohol preferably in the presence of a condensation catalyst such as 4-dimethylamine pyridine and a tertiary amine base such as triethylamine to afford the ester 11. Alternatively, the acid 10 and monoprotected diol may be coupled to afford 11 by treatment with a dehydration agent such as DCC. Alternatively, compound 10 may be first converted into an alkali metal salt such as the sodium, potassium, or lithium salt, which is then reacted with an alkyl halide which also contains a protected hydroxyl group in an polar solvent such as DMF to afford 11. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as methylene chloride, THF, DMF, or acetonitrile with or without an amine base such as pyridine or triethyl amine affords the compound of the formula IVA.

Scheme IX

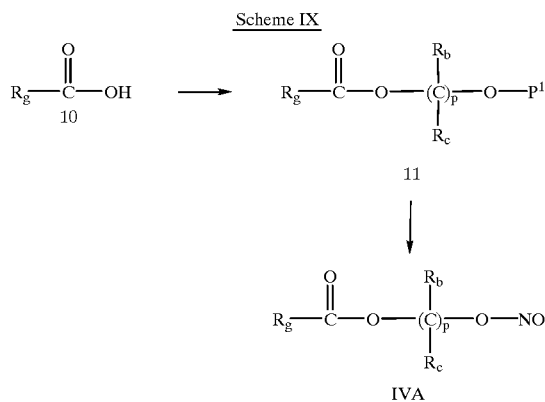

Nitroso compounds of formula (IV) wherein $R_g$ is defined as above and a S-nitrosylated ester is representative of the X group as defined above may be prepared according to Scheme X. An acid of the formula 10 is converted into the ester of the formula 12 by reaction with an appropriate protected thiol containing alcohol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as diethylether or THF. The mixed anhydride is then reacted with the protected thiol containing alcohol preferably in the presence of a condensation catalyst such as 4-dimethylamine pyridine. Alternatively, the acid 10 may be first converted to the acid chloride by treatment with oxalyl chloride in the presence of a catalytic amount of DMF. The acid chloride is then reacted with the protected thiol containing alcohol preferably in the presence of a condensation catalyst such as 4-dimethylamine pyridine and a tertiary amine base such as triethyl amine to afford the ester 12. Alternatively, the acid and protected thiol containing alcohol may be coupled to afford 12 by treatment with a dehydration agent such as DCC. Alternatively, compound 10 may be first converted into an alkali metal salt such as the sodium, potassium, or lithium salt, which is then reacted with an alkyl halide which also contains a protected thiol group in an polar solvent such as DMF to afford 12. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thiolesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile affords the compound of the formula IVB. Alternatively, this intermediate may be reacted with a stoichiometric quantity of sodium nitrite in aqueous acid affords the compound of the formula IVB Scheme X

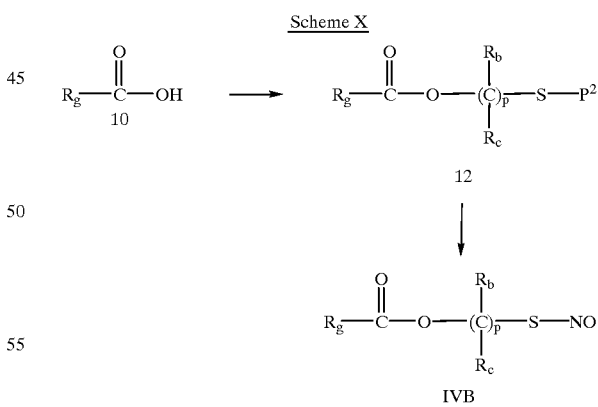

Nitroso compounds of formula (IV) wherein $R_g$ is defined as above and a 6-substituted sydnonimine is representative of the X group as defined above may be prepared according to Scheme XI. An acid of the formula 10 is converted into the carboximide of the formula IVC by reaction with a 6-W-substituted sydnonimine wherein W is as defined above. Preferred methods for the preparation of carboximides are initially forming the mixed anhydride via reaction of 10 with a chloroformate such as isobutylchloroformate in the presence of a non nucleophilic base such as triethylamine in an anhydrous inert solvent such as diethylether or THF. The mixed anhydride is then reacted with the 6-W-substituted sydnonimine to afford IVC. Alternatively, the acid 10 may be coupled to the 6-W-substituted sydnonimine afford IVC by treatment with a dehydration agent such as DCC. Alternatively, the acid 10 may be converted into an active ester by reaction with a suitably substituted phenol utilizing any of the conditions for ester formation described above, followed by reaction with a 6-W-substituted sydnonimine. Preferred 6-W-substituted sydnonimines are 1,2,6,4-oxatriazolium, 6-amino-6-morpholine and 1,2,6,4-oxatriazolium, 6-amino-6-(6-chloro-2-methyl -benzene) and preferred active esters are para-nitrophenyl, 2,4,5-trichlorophenyl, and pentafluorophenyl.

Scheme XI

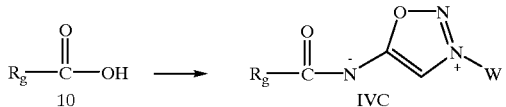

The compounds that donate, transfer or release nitric oxide can be any of those known to the art, including those mentioned and/or exemplified below.

Nitrogen monoxide can exist in three forms: NO⁻ (nitroxyl), NO• (nitric oxide) and NO⁺ (nitrosonium). NO• is a highly reactive short-lived species that is potentially toxic to cells. This is critical, because the pharmacological efficacy of NO depends upon the form in which it is delivered. In contrast to nitric oxide radical, nitrosonium and nitroxyl do not react with $O_2$ or $O_2^{-•}$ species, and are also resistant to decomposition in the presence of redox metals. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide (NO•) and charged nitric oxide species, particularly including nitrosonium ion (NO⁺) and nitroxyl ion (NO⁻). The reactive form of nitric oxide can be provided by gaseous nitric oxide. The nitric oxide releasing, delivering or transferring compounds, having the structure F-NO wherein F is a nitric oxide releasing, delivering or transferring moiety, include any and all such compounds which provide nitric oxide to its intended site of action in a form active for their intended purpose. As used here, the term "NO adducts" encompasses any of such nitric oxide releasing, delivering or transferring compounds, including, for example, S-nitrosothiols, S-nitroso amino acids, S-nitroso-polypeptides, and organic nitrites. It is contemplated that any or all of these "NO adducts" can be mono- or poly- nitrosylated at a variety of naturally susceptible or artificially provided binding sites for nitric oxide.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosated sugars, S-nitrosated-modified and unmodified oligonucleotides (preferably of at least 5, and more particularly 5–200, nucleotides); and an S-nitrosated hydrocarbon where the hydrocarbon can be a branched or unbranched, and saturated or unsaturated aliphatic hydrocarbon, or an aromatic hydrocarbon; S-nitroso hydrocarbons having one or more substituent groups in addition to the S-nitroso group; and heterocyclic compounds. S-nitrosothiols and the methods for preparing them are described in U.S. patent application Ser. No. 07/943,834, filed Sep. 14, 1992, Oae et al., *Org. Prep. Proc. Int.*, 15(3):165–198 (1983); Loscalzo et al., *J. Pharmacol. Exp. Ther.*, 249(3):726–729 (1989) and Kowaluk et al., *J. Pharmacol. Exp. Ther.*, 256:1256–1264 (1990), all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur group on an amino acid or amino acid derivative thereof) from various fictional classes including enzymes, such as tissue-type plasminogen activator(TPA) and cathepsin B; transport proteins, such as lipoproteins, heme proteins such as hemoglobin and serum albumin; and biologically protective proteins, such as the immunoglobulins and the cytokines. Such nitrosylated proteins are described in PCT Publ. Applic. No. WO 93/09806, published May 27, 1993. Examples include polynitrosylated albumin where multiple thiol or other nucleophilic centers in the protein are modified.

Further examples of suitable S-nitrosothiols include those having the structures:

(i) CH3[C($R_b$)($R_c$)]$_x$SNO wherein x equals 2 to 20 and $R_b$ and $R_c$ are as defined above;

(ii) HS[C($R_b$)($R_c$)]$_x$SNO wherein x equals 2 to 20; and (iii) ONS[C($R_b$)($R_c$)]$_x$Q wherein x equals 2 to 20 and Q is selected from the group consisting of fluoro, alkoxy, cyano, carboxamido, cycloalkyl, arylkoxy, alkylsulfinyl, arylthio, alkylamino, dialkylamino, hydroxy, carbamoyl, N-alkylcarbamoyl, N,N-dialkylcarbamoyl, amino, hydroxyl, carboxyl, hydrogen, nitro and aryl; and x, $R_b$ and $R_c$ are as defined above.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which may be used for this purpose include aqueous sulfuric, acetic and hydrochloric acids. Alternatively, they may be nitrosated by reaction with an organic nitrite such as tert-butyl nitrite, or an nitrosonium salt such as nitrosonium tetraflurorborate in an inert solvent.

Another group of such NO adducts are those wherein the compounds donate, transfer or release nitric oxide and are selected from the group consisting of compounds that include at least one ON—O—, ON—N— or ON—C— group. The compound that includes at least one ON—O—, ON—N— or ON—C— group is preferably selected from the group consisting of ON—O—, ON—N— or ON—C-polypeptides (the term "polypeptide" includes proteins and also polyamino acids that do not possess an ascertained biological function, and derivatives thereof); ON—O—, ON—N— or ON—C— amino acids (including natural and synthetic amino acids and their stereoisomers and racemic mixtures); ON—O—, ON—N— or ON—C—sugars; ON—O—, ON—N— or ON—C— modified and unmodified oligonucleotides (preferably of at least 5, and more particularly 5–200, nucleotides), ON—O—, ON—N— or ON—C-hydrocarbons which can be branched or unbranched, saturated or unsaturated aliphatic hydrocarbons or aromatic hydrocarbons; ON—O—, ON—N— or ON—C-hydrocarbons having one or more substituent groups in addition to the ON—O—, ON—N— or ON—C— group; and ON—O—, ON—N— or ON—C-heterocyclic compounds.

Another group of such adducts are N-oxo-N-nitrosoamines which donate, transfer or release nitric oxide and have a $R_1R_2$—N(O—M$^+$)—NO group wherein $R_1$ and $R_2$ include polypeptides, amino acids, sugars, modified and unmodified oligonucleotides, hydrocarbons where the hydrocarbon can be a branched or unbranched, and saturated or unsaturated aliphatic hydrocarbon or an aromatic hydrocarbon, hydrocarbons having one or more substituent groups and heterocyclic compounds. M$^+$ is a metal cation, such as, for example, a Group I metal cation.

Another group of such adducts are thionitrates which donate, transfer or release nitric oxide and have the structure $R_1$—(S)$_v$—NO wherein v is an integer of at least 2. $R_1$ is as described above for the N-oxo-N-nitrosoamines. Preferred are the dithiols wherein v is 2. Particularly preferred are those compounds where $R_1$ is a polypeptide or hydrocarbon with a pair or pairs of thiols that are sufficiently structurally proximate, i.e. vicinal, that the pair of thiols will be reduced to a disulfide. Those compounds which form disulfide species release nitroxyl ion (NO$^-$) and uncharged nitric oxide (NO•). Those compounds where the thiol groups are not sufficiently close to form disulfide bridges generally only provide nitric oxide as the NO$^-$ form but not as the uncharged NO• form.

Agents which stimulate endogenous NO synthesis such as L-arginine, the substrate for nitric oxide synthase, are also suitable for use in accordance with the invention.

When administered in vivo, the compositions may be administered in combination with pharmaceutical carriers and in dosages described herein.

The compositions of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Solid dosage forms for oral administration may include capsules, tablets, pills, powders, granules and gels. In such solid dosage forms, the active compounds may be admixed with at least one inert diluent such as sucrose, lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Dosage forms for topical administration of the composition can include creams, sprays, lotions, gels, ointments and the like. In such dosage forms the compositions of the invention can be mixed to form white, smooth, homogeneous, opaque lotions with, for example, benzyl alcohol 1% (wt/wt) as preservative, emulsifying wax, glycerin, isopropyl palmitate, lactic acid, purified water, sorbitol solution and polyethylene glycol 400. They can be mixed to form a white, smooth, homogeneous, opaque creams with, for example, benzyl alcohol 2% (wt/wt) as preservative, emulsifying wax, glycerin, isopropyl palmitate, lactic acid, purified water, and sorbitol solution. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g. gauze, can be impregnated with the compositions in solution, lotion, cream, ointment or other such form can also be used for topical application. The compositions can also be applied topically using a transdermal system, such as one of an acrylic-based polymer, adhesive with a resinous crosslinking agent impregnated with the composition and laminated to an impermeable backing.

Suppositories for rectal administration of the drug composition, such as for treating pediatric fever etc., can be prepared by mixing the drug with a suitable nonirritating excipient such as cocoa butter and polyethylene glycols which are solid at ordinary temperatures but liquid at the rectal temperature and will therefore melt in the rectum and release the drug.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1, 3-butanediol. Among the acceptable vehicles and solvents that may be employed are water, Ringer's solution, and isotonic sodium chloride solution. In addition, sterile, fixed oils are conventionally employed an a solvent or suspending medium.

While the compositions of the invention can be administered as a mixture of an NSAID and a nitric oxide donor, they can also be used in combination with one or more additional compounds which are known to be effective against the specific disease state that one is targeting for treatment.

The compositions of this invention can further include conventional excipients, i. e., pharmaceutically acceptable organic or inorganic carrier substances suitable for parenteral application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose sorbitol and/ or dextran. Optionally, the suspension may also contain stabilizers.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

Various delivery systems are known and can be used to administer a therapeutic compound or composition of the invention, e.g., encapsulation in liposomes, microparticles, microcapsules and the like.

The therapeutics of the invention can be formulated as neutral or salt forms. Pharmaceutically acceptable salts include, but are not limited to, those formed with free amino groups such as those derived from hydrochloric, phosphoric, sulfuric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The term "therapeutically effective amount," for the purposes of the invention, refers to the amount of the nitric oxide adduct which is effective to achieve its intended purpose. While individual needs vary, determination of optimal ranges for effective amounts of each nitric oxide adduct is within the skill of the art. Generally, the dosage required to provide an effective amount of the composition, and which can be adjusted by one of ordinary skill in the art will vary, depending on the age, health, physical condition, sex, weight, extent of disease of the recipient, frequency of treatment and the nature and scope of the disorder.

The amount of a given NSAID which will be effective in the treatment of a particular disorder or condition will depend on the nature of the disorder or condition, and can be determined by standard clinical techniques. Reference is again made to Goodman and Gilman, supra; The Physician's Desk Reference, Medical Economics Company, Inc., Oradell, N.J., 1995; and to Drug Facts and Comparisons, Facts and Comparisons, Inc., St. Louis, Mo., 1993. The precise dose to be employed in the formulation will also depend on the route of administration, and the seriousness of the disease or disorder, and should be decided according to the judgment of the practitioner and each patient's circumstances.

The amount of nitric oxide donor in a pharmaceutical composition may be in amounts of 0.1–10 times the molar equivalent of the NSAID. The usual daily doses of NSAIDs are 3–40 mg/kg body weight and the doses of nitric oxide donors in the pharmaceutical composition may be in amounts of 1–500 mg/kg body weight daily and more usually about 1–50 mg/kg. Effective doses may be extrapolated from dose-response curves derived from in vitro or animal model test systems and are in the same ranges or less than as described for the commercially available compounds in the Physician's Desk Reference, supra.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following non-limitative examples further describe and enable one of ordinary skill in the art to make and use the invention. Flash chromatography was performed on 40 micron silica gel (Baker).

EXAMPLE 1

Cholest-5-en-3β-O-nitroso alcohol

Cholesterol (0.242 g, 0.62 mmol) was dissolved in anhydrous methylene chloride (3 mL) and pyridine (0.103 g, 3.45 mmol) was added, followed by nitrosonium tetrafluoroborate (0.036 g, 0.31 mmol). After stirring for 1 hour at room temperature an additional nitrosonium tetrafluoroborate (0.099 g, 0.85 mmol) was added. The reaction mixture was stirred at room temperature for 16 hours. The solvent was evaporated and the residue was purified by flash chromatography on silica gel, deactivated with triethylamine, eluted methylene chloride to give 0.165 g (64% yield) of the title compound as a white solid. $^1$H NMR (CDCl$_3$), δ: 0.86 (d, 6 H), 0.92 (d, 3 H), 1.05–1.75 (m, 21 H), 1.80–2.01 (m, 6 H), 2.25–2.47 (m, 2 H (m, 1 H), 5 44 (m, 1 H).

EXAMPLE 2

N-(N-L-γ-glutamyl-S-Nitroso-L-cysteinyl)glycine

N-(N-L-γ-glutamyl-L-cysteinyl)glycine (100 g, 0.325 mol) was dissolved in deoxygenated water (200 ml) and 2N HCl (162 ml) at room temperature and then the reaction mixture was cooled to 0° C. With rapid stirring, a solution of sodium nitrite (24.4 g, 0.35 mol) in water (40 ml) was added and stirring with cooling of the reaction mixture was continued for approximately 1 hour after which time the pink precipitate which formed was collected by vacuum filtration. The filter cake was resuspended in chilled 40% acetone-water (600 ml) and collected by vacumm filtration. The filter cake was washed with acetone (2×200 ml) and ether (100 ml) and then dried under high vacuum at room temperature in the dark to afford the title compound as a pink powder. $^1$H NMR (D$_2$O) δ: 1.98 (m, 2H), 2.32 (t,2H), 3.67 (t, 1H), 3.82 (s 2H), 3.86 (dd, 1H), 3.98 (dd, 1H), 4.53 (m, 1H).

EXAMPLE 3

S-Nitroso-triphenylmethanethiol

Triphenylmethyl mercaptan (0.050 g, 0.18 mmol) was dissolved in anhydrous methylene chloride and cooled to 0° C. Tert-butyl nitrite (0.186 g, 1.80 mmol) was added and the resulting mixture was stirred at 0° C. for 30 min. The reaction mixture was allowed to warm to room temperature and stirred at room temperature for 1 hour. The solvent and excess of tert-butyl nitrite were evaporated to give the title compound as a green solid (0.054 g, 98%). $^1$H NMR (CDCl$_3$) δ: 7.13–7.18 (m, 4 H), 7.25–7.39 (m, 11_H).

EXAMPLE 4

4-O-Nitroso-1-(3-benzoyl-α-methylbenzeneacetic acid) butyl ester 4a. 4-Hydroxy-1-(3-benzoyl-α-methylbenzeneacetic acid) butyl ester 3-Benzoyl-α-methylbenzeneacetic acid (4 g, 16 mmol) and 100 μL DMF were dissolved in benzene (25 mL). Oxalyl chloride (1.6 mL, 18 mmol) was added dropwise. Stirring was continued for 2 hr before concentration to a syrup. Butanediol (9 mL, 100 mmol) and pyridine (1.67 mL, 21 mmol) were dissolved in CH$_2$Cl$_2$ (100 mL) and dioxane (15 mL) and cooled to 0° C. A solution of the acid chloride was added in CH$_2$Cl$_2$ (20 mL). The reaction mixture was stirred cold for 20 min then warmed to room temperature with stirring for 2 hr. The solution was washed 1×30 H$_2$O, 1 N HCl, satd NaHCO$_3$ and brine; dried over Na$_2$SO$_4$; and the volatiles were evaporated. The residue was filtered through a pad of silica gel eluting with 2:1 Hex:EtOAc to yield 4.8 g (91%) of hydroxy ester. $^1$H NMR (CDCl$_3$) δ: 7.41–7.81 (mult, 9H), 4.08–4.15 (mult, 2H), 3.79 (q, J=7.2 Hz, 1H), 3.59 (t, J=6.3 Hz, 2H), 1.53–1.69 (mult, 4H), 1.53 (d, J=7.2 Hz, 3H).

4b. 4-O-Nitroso-1-(3-benzoyl-α-methylbenzeneacetic acid) butyl ester

The product of Example 4a (1 g, 3.6 mmol) and pyridine (1.4 mL, 18 mmol) were dissolved in dichloromethane (15 mL) and cooled to −78° C. Nitrosonium tetrafluoroborate (840 mg, 7.2 mmol) was added and the solution was kept cold for 30 min. The reaction was warmed to room temperature with continued stirring for 1 hr. The mixture was diluted with dichloromethane and washed with 1N HCl, then brine. The solution was dried over sodium sulfate and evaporated. Chromatography on silica gel eluting with 9:1 Hexane:EtOAc gave 840 mg (76%) of the title compound.

$^1$H NMR (CDCl$_3$) δ: 7.41–7.80 (m, 9H), 4.65 (m, 1H), 4.11 (t, J=6.0 Hz, 2H), 3.79 (q, J=7.2 Hz, 1H), 1.65–1.72 (m, 4H), 1.53 (d, J=7.2 Hz, 3H Anal Calcd for C$_{20}$H$_{21}$NO$_5$: C, 67.59; H, 5.96; N, 3.94. Found: C, 66.72; H, 5.95; N, 2.93

EXAMPLE 5

4-O-Nitroso-4-methyl-1-(3-benzoyl-α-methylbenzeneacetic acid) pentyl ester 5a. 4-Hydroxyl-4-methyl-1-(3-benzoyl-α-methylbenzeneacetic acid) pentyl ester 3-Benzoyl-a-methylbenzeneacetic acid (1.99 g, 7.7 mmol) in methylene chloride (20 mL) under nitrogen and cooled over ice was treated successively with oxalyl chloride (1.36 mL, 15.7 mmol) and dimethylformamide (5 drops). A vigorous gas evolution was noted and the reaction mixture was stirred with slow warming and then overnight at ambient temperature. The volatile materials were removed in vacuo and the residue dissolved in methylene chloride (10 mL) and added dropwise to a precooled mixture of 2-methyl-2,5-pentanediol (3.7 g, 31 mmol) and pyridine (0.69 mL, 8.6 mmol) also in methylene chloride (10 mL) under a nitrogen atmosphere. The reaction mixture was stirred under nitrogen with slow warming and then overnight at ambient temperature. The solution was washed successively with 2N hydrochloric acid and 2N sodium hydroxide, dried over anhydrous sodium sulfate, filtered and concentrated in vacuo. The residual oil was subjected to column chromatography using ethyl acetate/hexane (1:2). The product was isolated as an oil in 76% yield (2.1 g). $^1$H NMR (CDCl$_3$) δ: 7.77–7.81 (m, 3H), 7.64–7.43 (m, 6H), 4.18–4.03 (m, 2H), 3.80 (q, J=7.2 Hz, 1H), 1.62–1.71 (m, 2H), 1.54 (d, J=7.2 Hz, 3H), 1.42–1.35 (m, 2H), 1.16 (s, 6H). Anal calcd for C$_{22}$H$_{26}$O$_4$: C, 74.55; H, 7.39. Found: C, 74.26; H. 7.43.

5b. 4-O-Nitroso-4-methyl-1-(3-benzoyl-α-methylbenzeneacetic acid) pentyl ester

A solution of the product of example 5a (0.4 g, 1.13 mmol) and pyridine (456 mL, 5.6 mmol) in methylene chloride (4 mL) was cooled to −78° C. and nitrosonium tetrafluoroborate (262 mg, 2.26 mmol) added. The reaction mixture was stirred at −78° C. for 3 hours, washed with water and dried over sodium sulfate. After filtration and evaporation of the solvent the residual oil was subjected to column chromatography using ethyl acetate/hexane/triethylamine (18:80:2). The title compound was isolated as an oil in 58% yield (0.25 g). $^1$H NMR (CDCl$_3$) δ: 7.41–7.80 (m, 9H), 4.02–4.17 (m, 2H), 3.79 (q, J=7.2 Hz, 1H), 1.73–1.79 (m, 2H) 1.62–1.69 (m, 2H), 1.52–1.55 (m, 9H).

EXAMPLE 6

3-S-Nitroso-3-methyl-1-(3-benzoyl-α-methylbenzeneacetic acid) butyl ester 6a. 3-Mercapto-3-methyl-1-(3-benzoyl-α-methylbenzeneacetic acid) butyl ester To 3-Benzoyl-α-methylbenzeneacetic acid (529 mg, 2 mmol) in benzene (5 mL) containing 5 ml of DMF was added oxalyl chloride (200 ml 2.2 mmol) dropwise. The reaction mixture was stirred 1.5 hr and then concentrated in vacuo to a syrup. The crude acid chloride was dissolved in dichloromethane (10 mL) and 3-mercapto-3-methyl butanol (Sweetman et al. *J. Med. Chem.* 14, 868 (1971) (350 mg, 2.2 mmol) was added followed by pyridine (180 ml, 2.2 mmol). The reaction was stirred at room temperature for 1 h and then it was diluted with dichloromethane and wash with 1N HCl, followed by saturated sodium bicarbonate, and then brine. The organic phase was dried over sodium sulfate, concentrated in vacuo, and the residue was chromatographed on silica gel eluting with 9:1 hexane:ethyl acetate to afford 640 mg (90%) of the product. $^1$H NMR (CDCl$_3$) δ: 7.41–7.81 (m, 9H), 4.28 (t, J=7.1 Hz, 2H), 3.78 (q, J=7.2 Hz, 1H), 1.88 (t, J=7.0 Hz, 2H), 1.69 (s, 1H), 1.54 (d,J=7.3 Hz, 3H), 1.35 (s, 3H), 1.34 (s, 3H).

6b. 3-S-Nitroso-3-methyl-1-(3-benzoyl-α-methylbenzeneacetic acid) butyl ester

To a solution of the product of Example 6a (105 mg, 0.3 mmol) in dichloromethane (4 mL) was added tert-butyl nitrite (70 mg, 0.6 mmol) in a dropwise fashion. The mixture was stirred at room temperature for 30 min. The solvent and excess reagent were remove in vacuo to give 113 mg (quantitative) of the title compound. $^1$H NMR (CDCl$_3$) δ: 7.44–7.81 (m, 9H), 4.29 (t, J=6.9 Hz, 2H), 3.77 (q, j=7.2 Hz, 1H), 2.51 (t, j=6.9 Hz, 2H), 1.841 (s, 3H), 1.836 (s, 3H), 1.53 (d, J=7.2 3H).

EXAMPLE 7

4-O-Nitroso-1-((S)-6-methoxy-α-methyl-2-naphthaleneacetic acid) butyl ester 7a. (S)-6-methoxy-α-methyl-2-naphthaleneacetic acetyl chloride Under a nitrogen atmosphere, oxalyl chloride (4.13 g, 30 mmol) was combined with methylene chloride (30 mL) and the resulting mixture was cooled to 0° C. Dimethylformamide (10 drops) was added and after 5 minutes of stirring, a suspension of (S)-6-methoxy-α-methyl-2-naphthaleneacetic acid (3.00 g, 13 mmol) in methylene chloride (30 mL) was added dropwise over a 30 minute period. The reaction mixture was allowed to warm to room temperature and stirred overnight. The solvent was evaporated in vacuo to give the product in a quantitative yield. $^1$H NMR (CDCl$_3$) δ: 1.5 (d, 3 H), 3.91 (s, 1 H), 4.21 (q, 1 H), 7.09–7.14 (m, 1 H), 7.15 (d, 1 H), 7.42 (dd, 1 H), 7.68 (s, 2 H), 7.71 (s, 1H).

7b. 4-Hydroxy-1-((S)-6-methoxy-α-methyl-2-naphthaleneacetic acid) butyl ester

Under a nitrogen atmosphere, 1,4-butanediol (5.30 mL, 60 mmol) and pyridine (0.95 g, 12 mmol) were combined in methylene chloride (20 mL). The resulting solution was stirred for 5 minutes and then cooled to 0° C. A solution of the product of Example 7a (3.0 g, 12 mmol) in methylene chloride (15 ml) was added dropwise over 30 minute period. After stirring for 20 hours at room temperature, the reaction mixture was diluted with ethyl acetate and washed with 1N hydrochloric acid. The organic phase was dried over anhydrous sodium sulfate and concentrated in vacuo. The residue was purified by flash chromatography on silica gel using hexane/ethyl acetate (1:1 to 1:3) to afford 3.09 g (79% yield) of the product as a colorless oil. $^1$H NMR (CDCl$_3$) δ: 1.47–1.68 (m, 4H, overlapping with a doublet at 1.57, 3H), 3.55 (t, 2H), 3.84 (q, 1H), 3.91 (s, 3H), 4.11 (t, 2H), 7.11 (m, 2H), 7.15 (d, 1H), 7.42 (dd, 1H), 7.67 (s, 1H), 7.70 (d, 2H).

7c. 4-O-Nitroso-1-((S)-6-methoxyl-α-methyl-2-naphthaleneacetic acid) butyl ester The product of Example 7b (0.209 g, 0.69 mmol) was dissolved in anhydrous methylene chloride (4 mL) and pyridine (0.273 g, 3.45 mmol) was added. The resulting solution was cooled to −78° C. and nitrosonium tetrafluoroborate (0.161 g, 1.38 mmol) was added in one portion. The reaction mixture was stirred for 1 hour at −78° C. The solvent was evaporated in vacuo and the residue was purified by flash chromatography on silica gel, deactivated with triethylamine, eluted with ethyl acetate/hexane (1:2) to give 0.180 g (79% yield) of the title compound as an oil. $^1$H NMR (CDCl$_3$) δ: 1.58 (d, 3H), 1.64–1.69 (m, 4H), 3.85 (q, 1H), 3.92 (s, 3H), 4.11 (t, 2H), 4.60 (s, 2H), 7.10–7.13 (m, 1H), 7.15 (d, 1H), 7.39 (dd, 1H), 7.70 (d, 2H).

EXAMPLE 8

4-O-Nitroso-1-(1-)4-chlorobenzoyl)-5-methoxy-2-methyl-1H-indole-3-acetic acid) butyl ester 8a. 4-Hydroxy-1-(1-(4-chlorobenzoyl)-5-methoxy-2-methyl-1H-indole-3-acetic acid) butyl ester A stirred suspension of 1(4-chlorobenzoyl)5-methoxy-2-methylindoyl)-3-acetic acid (3.7 g, 10.5 mmol) in methylene chloride (20 mL) under nitrogen and cooled over ice was treated successively with oxalyl chloride (1.8 mL, 20.6 mmol) and dimethylformamide (10 drops). A vigorous gas evolution was noted and the reaction mixture was stirred with gradual warming to room temperature and then at ambient for a total of 5 hours. The volatile materials were removed in vacuo and the residue dissolved in dichloromethane (10 mL) and added dropwise to a precooled mixture of 1,4-butanediol (4.7 g, 51.7 mmol) and pyridine (0.92 mL, 11.4 mmol) also in methylene chloride (10 mL). The reaction mixture was stirred with slow warming and then for 5 hours at ambient temperature under a nitrogen atmosphere. The solution was washed with 2N hydrochloric acid, saturated sodium bicarbonate, dried over anhydrous sodium sulfate, filtered and concentrated in vacuo. The residual oil was subjected to column chromatography using ethyl acetate/hexane (1:2). The product was isolated as an oil in 75% yield (3.3 g ) which solidified on standing $^1$H NMR (CDCl$_3$) δ: 7.67 (d, J=8.4 Hz, 2H), 7.47 (d, J=8.5 Hz, 2H), 6.97 (d, J=2.5 Hz, (1H), 6.87 (d, J=9 Hz, 1H), 6.67 (dd, J=2.5 Hz, 9 Hz, 1H), 4.13 (t, J=6.4 Hz, 2H), 3.83 (s, 3H), 3.66 (s, 2H), 3.59 (t, J=6.4 Hz, 2H), 2.38 (s, 3H), 1.51–1.75 (m, 4H). Anal calcd for C$_{23}$H$_{24}$ClNO$_5$: C, 64.26; H, 5.63; N, 3.26. Found: C, 64.08; H, 5.60; N, 3.18.

8b. 4-O-Nitroso-1-(1-(4-chlorobenzoyl)-5-methoxy-2-methyl-1H-indole-3-acetic acid) butyl ester A stirred solution of the product of Example 8a (1 g, 2.3 mmol), and pyridine (0.90 mL, 11.6 mmol) in methylene chloride (15 mL) at −78° C. under a nitrogen atmosphere was treated with nitrosonium tetrafluoroborate (0.54 g, 4.6 mmol). The reaction mixture was stirred at −78° C. for 3.5 hours, washed with water, dried with anhydrous sodium sulfate and the solvent removed in vacuo. The residual oil was subjected to column chromatography using ethyl acetate/hexane (1:3). The product was isolated as a yellow oil in 69% yield (0.73 g). $^1$H NMR (CDCl$_3$) δ: 7.66 (d, J=8.5 Hz, 2 Hz), 7.47 (d, J=8.5 Hz, 2H), 6.95 (d, J=2.5 Hz, 1H), 6.85 (d, J=5 Hz, 1H), 6.66 (dd, J=2.5 Hz, 6.5 Hz, 1H), 4.66 (br s, 2H), 4.16 (t, J=6.6 Hz, 2H), 3.83 (s, 3H), 3.66 (s, 2H), 2.39 (s, 3H), 1.65–1.80 (m, 4H). Anal calcd for C$_{23}$H$_{23}$ClN$_2$O$_6$: C, 60.2; H, 5.05; N, 6.1. Found: C, 59.93; H, 4.87; N, 5.85.

EXAMPLE 9

3-O-Nitroso-1-(1-(4-chlorobenzoyl)-5-methoxy-2-methyl-1H-indole-3-acetic acid) butyl ester 9a. 3-Hydroxy-1-(1-(4-chlorobenzoyl)-5-methoxy-2-methyl-1H-indole-3-acetic acid) butyl ester A stirred suspension of 1-(4-chlorobenzoyl)-5-methoxy-2-methyl-1H-indole-3-acetic acid (5 g, 13.9 mmol) in methylene chloride (25 mL) under nitrogen and cooled over ice was treated successively with oxalyl chloride (2.44 mL, 28 mmol) and dimethylformamide (10 drops). A vigorous gas evolution was noted and the reaction mixture was stirred with gradual warming for a total of 5 hours. The volatile materials were removed in vacuo and the residue dissolved in methylene chloride (15 mL) and added dropwise to a precooled mixture (+/−)-1,3-butanediol (8.83 g, 98 mmol) and pyridine (1.24 mL, 15.4 mmol) also in dichloromethane (10 mL). The reaction mixture was stirred with slow warming and then over the weekend at ambient temperature under a nitrogen atmosphere. The solution was washed with 2N hydrochloric acid, saturated sodium bicarbonate, dried over anhydrous sodium sulfate, filtered and concentrated in vacuo. The residual oil was subjected to column chromatography using ethyl acetate/hexane (1:1). The product was isolated as an oil which solidified on standing in 75% yield (4.5 g). $^1$H NMR indicated that the desired product was contaminated with an isomer and so it was recrystalised three times from diethyl ether/hexanes to give the desired product as a solid in 15% yield (0.9 g). $^1$H NMR (CDCl$_3$) δ: 7.66 (d, J=8.5 Hz, 2H), 7.43 (d, J=8.5 Hz, 2H), 6.95 (d, J=2.4 Hz, 1H), 6.86 (d, J=9 Hz, 1H), 6.67 (dd, J=9 Hz, 2.5 Hz), 4.30–4.39 (m, 1H), 4.15–4.4 (m, 1H), 3.83 (s, 3H), 3.75–3.85 (m, 1H), 3.67 (s, 2H), 2.38 (s, 3H), 1.95 (s, 1H), 1.65–2.8 (m, 2H), 1.16 (d, J=6.3 Hz, 3H). Anal calcd for C$_{23}$H$_{24}$ClNO$_5$: C, 64.26; H, 5.63; N, 3.26. Found: C, 64.29; H, 5.53; N, 3.18.

9b 3-O-Nitroso-1-(1-(4-chlorobenzoyl)-5-methoxy-2-methyl-1H-indole-3-acetic acid) butyl ester A stirred solution of the product of Example 9a (0.15 g, 0.34 mmol), and pyridine (0.14 mL, 1.7 mmol) in dichloromethane (2 mL) at −78° C. under a nitrogen atmosphere was treated with nitrosonium tetrafluoroborate (0.08 g, 0.7 mmol). The reaction mixture was stirred at −78° C. for 3.5 hours, washed with water, dried with anhydrous sodium sulfate and the solvent removed in vacuo. The residual oil was subjected to column chromatography using ethyl acetate/hexane (1:3). The title compound was isolated as a yellow oil in 79% yield (0.125 g). $^1$H NMR (CDCl$_3$) δ: 7.66 (d, J=8.5 Hz, 2H), 7.47 (d, J=8.5 Hz), 6.95 (d, J=2.3 Hz, 1H), 6.86 (d, J=9 Hz, 1H), 6.67 (dd, J=9 Hz, 2.5 Hz), 5.52 (sextet, J=6.5 Hz, 1H), 4.06–4.24 (m, 2H), 3.83 (s, 3H), 3.65 (s, 2H), 2.38 (s, 3H), 2.05 (q, J=4 Hz, 2H), 1.37 (d, J=6.5 Hz).

EXAMPLE 10

4-O-Nitroso-4 methyl-1-(1-(4-chlorobenzoyl)-5methoxy-2-methyl-1H-indole-3-acetic acid) pentyl ester 10a. 4-Hydroxy-4 methyl-1-(1-(4-chlorobenzoyl)-5-methoxy-2-methyl-1H-indole-3-acetic acid) pentyl ester A stirred suspension of 1-(4-chlorobenzoyl)-5-methoxy-2-methyl-1H-indole-3-acetic acid (2.8 g, 7.7 mmol) in methylene chloride (25 mL) under nitrogen and cooled over ice was treated successively with oxalyl chloride (1.36 mL, 15.7 mmol) and dimethylformamide (5 drops). A vigorous gas evolution was noted and the reaction mixture was stirred over ice for 30 min and then at room temperature for 3 hours. The volatile materials were removed in vacuo and the residue dissolved in methylene chloride (15 mL) and added dropwise to a precooled mixture of 2-methyl-2,5-pentanediol (3.7 g, 31 mmol) and pyridine (0.69 mL, 8.6 mmol) also in methylene chloride (10 mL). The reaction mixture was stirred under nitrogen with slow warning and then overnight at ambient temperature under a nitrogen atmosphere. The solution was washed with 2N hydrochloric acid, dried over anhydrous sodium sulfate, and filtered to give an oil which was concentrated in vacuo. The residual oil was subjected to column chromatography using ethyl acetate/hexane (1:2) The product was isolated as an oil which solidified on standing in 100% yield (3.6 g). $^1$H NMR (CDCl$_3$) δ: 7.69 (d, J=8.9 Hz, 2H), 7.47 (d, J=8.9 Hz, 2H), 6.98 (d, J=2.5 Hz, 1H), 6.87 (d, J=9 Hz, 1H), 6.67 (dd, J=9 Hz, 2.5 Hz), 4.09–4.14 (m, 2H), 3.83 (s, 3H), 3.66 (s, 3H), 2.39 (s, 3H), 1.62–1.73 (m, 2H), 1.37–1.43 (m, 2H), 1.14 (s, 6H). Anal calcd for $C_{25}H_{28}ClNO_5$: C, 65.57; H. 6.16; N, 3.06. Found: C, 65.35; H, 6.25; N, 3.10.

10b. 4-O-Nitroso-4 methyl-1-(1-(4-chlorobenzoyl)-5-methoxy-2-methyl-1H-indole-3-acetic acid) pentyl ester A solution of the product of Example 10a (0.2 g, 0.44 mmol) and pyridine (176 mL, 2.2 mmol) in methylene chloride (2 mL) was cooled over dry ice and nitrosonium tetrafluoroborate (101 mg, 0.87 mmol) added. The reaction mixture was stirred at −78° C. for 3 hours, allowed to stand at the same temperature overnight, washed with water and dried over sodium sulfate. After filtration and evaporation of the solvent the residual oil was subjected to column chromatography (twice) using ethyl acetate/hexanes/triethylamine (25:73:2). The product was isolated as an oil in 42% yield (0.09 g). $^1$H NMR (CDCl$_3$) δ: 7.66 (d, J=7.5 Hz, 2H), 7.47 (d, J=7.5 Hz, 2H), 6.96 (d, J=2.5 Hz, 1H), 6.86 (d, J=9 Hz, 1H), 6.66 (dd, J=7.5 Hz, 2.5 Hz), 4.11 (t, J=6 Hz, 2H), 3.83 (s, 3H), 3.66 (s, 2H), 2.39 (s, 3H), 1.75–1.81 (m, 2H), 164–1.72 (m, 2H), 1.51 (s, 6H).

EXAMPLE 11

3-S-Nitroso-3-methyl-1-(α-methyl-4-(2-methylpropyl)benzeneacetic acid) butyl ester A solution of α-methyl-4-(2-methylpropyl)benzeneacetic acid (1.52 g, 7.4 mmol) in methylene chloride (15 mL) cooled over ice and under nitrogen, was treated successively with oxalyl chloride (1.29 mL, 1.88 g, 14.8 mmol) and dimethylformamide (5 drops). The resultant solution was stirred over ice for 30 min and then at ambient temperature for 2 hours. The excess volatile materials were removed in vacuo and the residue, dissolved in methylene chloride (5 mL), added to a precooled solution of pyridine (0.54 mL, 6.7 mmol) and 3-mercapto-3-methylbutanol (0.8 g, 6.7 mmol) in methylene chloride (15 mL). The reaction mixture was stirred over ice for 30 min and then at ambient temperature for 3 hours. The solution was then diluted with additional methylene chloride and washed with 2N hydrochloric acid, saturated sodium bicarbonate and brine and the organic phase dried with sodium sulfate, filtered and the solvent removed in vacuo. The residual oil was subjected to column chromatography using ethyl acetate/hexane (1:3). The product was isolated as an oil in 68% yield (1.4 g). $^1$H NMR (CDCl$_3$) δ: 7.18 (d, J=7.5 Hz, 2H), 7.09 (d, 7.5 Hz, 2H), 4.25 (t, J=6.5 Hz, 2H), 3.67 (q, J=7 Hz, 1H), 2.44 (d, J=7.8 Hz, 2H), 1.77–1.9 (m, 3H), 1.48 (d, J=7 Hz, 3H), 1.32 (s, 6H), 0.89 (d, J=6.6 Hz, 6H).

11b. 3-S-Nitroso-3-methyl-1-(α-methyl-4-(2-methylpropyl)benzeneacetic acid) butyl ester A solution of the product of Example 11a (0.4 g, 1.2 mmol) in methylene chloride (8 mL) under nitrogen was treated with tert butyl nitrite (0.62 mL, 0.53 g, 5 mmol). After stirring for 1 hour at ambient temperature the volatile materials were removed in vacuo. The residual green oil was subjected to column chromatography using ethyl acetate/hexanes (1:19). The product was isolated asgreen oil in 65% yield (0.25 g). $^1$H NMR (CDCl$_3$) δ: 7.0 (d, J=7.5 Hz, 2H), 7.10 (d, J=7.5 Hz, 2H), 4.27 (t, J=6.9 Hz, 2H), 3.66 (q, J=7.2 Hz, 1H), 2.49 (t, J=6.6 Hz, 2H), 2.44 (d, J=72 Hz, 2H), 1.8–1.9 (m, 1H), 1.81 (s, 3H), 1.80 (s, 3H), 1.48 (d, J=7.2 Hz, 3H), 0.89 (d; J=6.6 Hz, 6H).

EXAMPLE 12

4-O-Nitroso-1-(α-methyl-4-(2-methylpropyl) benzeneacetic acid) butyl ester 12a. 4-Hyroxy-1-(α-methyl-4-(2-methylpropyl) abenzeneacetic acid) butyl ester α-Methyl-4-(2-methylpropyl)benzeneacetic acid (4 g, 19 mmol) and 10 uL DMF were dissolved in benzene (30 mL). Oxalyl chloride was added dropwise. Stirring was continued for 2 hr before concentration to a syrup. Butanediol (9 mL, 100 mmol) and pyridine (1.67 mL, 21 mmol) were dissolved in dichloromethane (100 mL) and dioxane (15 mL) and cooled to 0° C. A solution of the acid chloride was added in dichloromethane (20 mL). The reaction mixture was stirred cold for 20 min then warmed to room temperature with stirring for 2 hr. The solution was washed H$_2$O, 1 N HCl, satd Sodium bicarbonate and finally brine; dried over sodium sulfate; and evaporated. The residue was filtered through silica gel eluting with 2:1 hexane:EtOAc to yield 4.8 g (91%) of the product. $^1$H NMR (CDCl$_3$) δ: 7.19 (d, J=6.2 Hz, 2H), 7.08 (d, J=8.2 Hz, 2H),4.07–4.12 (m, 2H), 3.68 (q, J=7.1 Hz, 1H), 3.58 (t, J=6.3 Hz, 1H), 2.44 (d, J=7.2 Hz, 2H), 1.84 (sept, J=6.8 Hz, 1H), 1.50 –1.69 (m, 4H), 1.48 (d, J=7.2 Hz, 3H), 0.88 (d, J=6.6 Hz, 6H). Anal Calcd for $C_{17}H_{26}O_3$: C, 73.34; H, 9.41. Found: C, 73.17; H, 9.67

12b. 4-O-Nitroso-1-(α-methyl4-(2-methylpropyl) benzeneacetic acid) butyl ester

The product of Example 12a (1 g, 3.6 mmol) and pyridine (1.4 mL, 18 mmol) were dissolved in dichloromethane (15 mL) and cooled to −78° C. Nitrosonium tetrafluoroborate (840 mg, 7.2 mmol) was added and the solution was kept cold for 30 min. The reaction was warmed to room temperature with continued stirring for 1 hr. The mixture was diluted with dichloromethane and washed successively with 1N HCl, H$_2$O, and brine. The solution was dried over sodium sulfate and evaporated. Chromatography on silica gel eluting with 9:1 hexane:EtOAc gave 840 mg (76%) of the title compound. $^1$H NMR (CDCl$_3$) δ: 7.18 (d, J=8.1 Hz, 2H), 7.08 (d, J=8.1 Hz, 2H), 4.62 (m, 2H), 4.07–4.12 (m, 2H), 3.68 (q, J=7.1 Hz, 1H), 2.44 (d, J=7.2 Hz, 2H), 1.84 (sept, J=6.7 Hz, 1H), 1.64–1.68 (m, 4H), 1.48 (d, J=7.2 Hz, 3H), 0.88 (d, J=6.6 Hz, 6H).

EXAMPLE 13

4-O-Nitroso-1-(2-Fluoro-α-methyl-biphenylacetic acid) butyl ester 13a. 2-Fluoro-α-methyl-biphenylacetic acid chloride Under a nitrogen atmosphere, oxalyl chloride (3.8 g, 30 mmol) was combined with methylene chloride (30 mL). The resulting mixture was cooled to 0° C. and dimethylformamide (10 drops) was added. After 5 minutes of stirring a solution of 2-fluoro-α-methyl-biphenylacetic acid (3.0 g, 12 mmol) in methylene chloride (30 mL) was added dropwise over a 30 minute period. The reaction mixture was allowed to warm to room temperature and stirred overnight. The solvent was evaporated to give the product in a quantitative yield as a yellow solid. $^1$H NMR (CDCl$_3$) δ: 1.58 (d, 3 H), 4.20 (q, 1 H), 7.11 (t, 2 H), 7.33–7.47 (m, 4 H), 7.54 (d, 2 H).

13b. 4-Hydroxy-1-(2-Fluoro-α-methyl-biphenylacetic acid) butyl ester

Under a nitrogen atmosphere, 1,4-butanediol (5.30 mL, 60 mmol) and pyridine (0.95 g, 12 mmol) were combined in methylene chloride (20 mL). The resulting solution was stirred for 5 minutes and then cooled to 0° C. A solution of the product of Example 13a (3.0 g, 12 mmol) in methylene chloride (15 ml) was added dropwise over 30 minute period. After stirring for 20 hours at room temperature, the reaction mixture was diluted with ethyl acetate and washed with 1N hydrochloric acid. The organic phase was dried over anhydrous sodium sulfate and concentrated in vacuo. The residue was purified by flash chromatography on silica-gel eluting with methylene chloride/hexane (2:1) to give 1.66 g (44%) of the product as a colorless oil. $^1$H NMR (CDCl$_3$) δ: 1.56 (d, 3 H), 1.61–1.77 (m, 4 H), 3.63 (t, 2 H), 3.75 (q, 1 H), 4.14 (t, 2 H), 7.14 (t, 2 H), 7.27–7.45 (m, 4 H), 7.53 (d, 2 H).

13c. 4-O-Nitroso-1-(2-Fluoro-α-methyl-biphenylacetic acid) butyl ester

The product of Example 13b (0.190 g, 0.60 mmol) was dissolved in anhydrous methylene chloride (4 mL) and pyridine (0.237 g, 3.00 mmol) was added. The resulting solution was cooled to −78° C. and nitrosonium tetrafluoroborate (0.084 g, 0.72 mmol) was added. The reaction mixture was stirred for 1 hour at −78° C. and an additional nitrosonium tetrafluoroborate (0.047 g, 0.40 mmol) was added. After 30 minutes of stirring at −78° C., the solvent was evaporated in vacuo and the residue was purified by flash chromatography on silica gel, deactivated with triethylamine, eluted with methylene chloride/hexane (3:1) to give 0.117 g (57% yield) of the title compound. $^1$H NMR (CDCl$_3$) δ: 1.54 (d, 3 H), 1.68–1.83 (m, 4 H), 3.75 (q, 1 H), 4.14 (t, 2 H), 4.67 (s, 2 H), 7.14 (t, 2 H), 7.34–7.48 (m, 4 H), 7.54 (d, 2 H).

EXAMPLE 14

4-O-Nitroso-1-(2-Fluoro-α-methyl-biphenylacetic acid) thiobutyl ester

14a. 1-tert-Butyldimethylsilyloxy-4chloro-butanol

4-Chloro-1-butanol (5.43 g, 50 mmol) was dissolved in dimethylformamide (50 mL) and tert-butyldimethylsilylchloride (7.54 g, 50 mmol) was added, followed by imidazole (3.4 g, 50 mmol). After 24 hours of stirring at room temperature, the reaction mixture was diluted with hexane, washed with water and brine and dried over anhydrous sodium sulfate. The solvent was evaporated to give colorless liquid which was purified by chromatography on silica gel eluting with hexane/ethyl acetate (30:1) to give the product (7.26 g, 56%). $^1$H NMR (CDCl$_3$) δ: 0.05 (s, 6H), 0.89 (s, 9 H), 1.64–1.68 (m, 2H), 1.82–1.86 (m, 2H), 3.57 (t, 2H), 3.64 (t, 2 H).

14b. 4-tert-Butyldimethylsilyloxy-1-acetyl-thiobutyl ester

Under a nitrogen atmosphere, potassium thioacetate (0.53 g, 4.7 mmol) was dissolved in dimethylformamide (12 mL) and cooled to 0° C. A solution of the product of Example 14a (1.01 g, 3.91 mmol) in dimethylformamide (14 mL) was added. After 24 hours of stirring at room temperature, the solvent was evaporated and the residue was partitioned between hexane and water (1:3). The organic layer was concentrated in vacuo to give the product (0.820 g, 71%) as a yellow liquid. $^1$H NMR (CDCl$_3$) δ: 0.04 (s, 6H), 0.88 (s, 9 H), 1.57–1.64 (m, 4H), 2.32 (s, 3H), 2.89 (2H), 3.61 (t, 2 H).

14c. 4-tert-Butyldimethylsilyloxy-1-butane thiol

The product of Example 14b (5.7 g, 19.2 mmol) was dissolved in methanol (30 mL) and degassed with nitrogen gas for 30 minutes. Potassium carbonate (2.92 g, 21.1 mmol) was added in one portion. After 1 hour of stirring at room temperature, the solvent was evaporated and the residue was partioned between hexane and water. The organic layer was dried over anhydrous sodium sulfate and concentrated in vacuo to give the product (3.2 g, 66%). $^1$H NMR (CDCl$_3$) δ: 0.05 (s, 6H), 0.89 (s, 9 H), 1 34 (t, 1H), 1.61–1.68 (m, 4H), 2.51–2.57 (q, 2H), 3.62 (t, 2 H).

14d. 4-tert-Butyldimethylsilyloxy-1-(2-Fluoro-α-methyl-biphenylacetic acid) thiobutyl ester The product of Example 14c (1.37 g, 5.4 mmol) was combined with pyridine (0:142 g, 1.8 mmol) in methylene chloride (5 mL) and the resulting solution was cooled to 0° C. A solution of the product of Example 13a (0.500 g, 1.8 mmol) in methylene chloride (4 mL) was added dropwise. After 22 hours of stirring at room temperature, the reaction mixture was diluted with ethyl acetate and washed with 1N hydrochloric acid. The organic layer was dried over anhydrous sodium sulfate and concentrated in vacuo to give the product (0.526 g, 59%). $^1$H NMR (CDCl$_3$) δ: 0.04 (s, 6H), 0.89 (s, 9H), 1.56 (d, 3H), 1.57–1.62 (m, 4H), 1.88–2.29 (M, 2H), 3.61 (t, 2H), 7.15 (t, 2H), 7.37–7.44 (m, 4H), 7.54 (d, 2 H).

14e. 4-Hydroxy-1-(2-Fluoro-α-methyl-biphenylacetic acid) thiobutyl ester

The product of Example 14d (0.320 g, 0.64 mmol) was dissolved in the mixture of glacial acetic acid (0.5 mL), water (1 mL), and tetrahydrofuran (5 mL). The resulting solution was stirred for 24 hours at room temperature. The solvent was evaporated and the residue was partitioned between methylene chloride and water. The organic layer was washed with saturated sodium bicarbonate solution and brine, and dried over anhydrous sodium sulfate. The solvent was evaporated to give the product (0.235 g, 100%). $^1$H NMR (CDCl$_3$) δ: 1.57 (d, 3H), 1.58–1.69 (m, 4H), 2.87–2.93 (m, 2H), 3.63 (t, 2H), 3.84–3.92 (q, 1H), 7.14 (t, 2H), 7.37–7.44.(m, 4H), 7.54 (d, 2 H).

14f. 4-O-Nitroso-1-(2-Fluoro-α-methyl-biphenylacetic acid) thiobutyl ester

The product of Example 14e (0.235 g, 0.61 mmol) was dissolved in anhydrous methylene chloride (3 mL) and pyridine (0.097 g, 1.23 mmol) was added. The resulting solution was cooled to −78° C. and nitrosonium tetrafluoroborate (0.144 g, 1.23 mmol) was added in one portion. The reaction mixture was stirred for 1 hour at −78° C., the solvent was evaporated, and the residue was purified by chromatography on silica gel eluted with hexane/ethyl acetate (10:1) to give the title compound (0.110 g, 44%). $^1$H NMR (CDCl$_3$) δ: 157 (d, 3H), 1.58–1.80 (m, 4H), 3.85–3.93 (q, 1H), 4.69 (t, 2H), 7.14 (t, 2H), 7.37–7.44 (m, 4H), 7 55 (d, 2 H).

EXAMPLE 15

4-O-Nitroso-2-methyl-N-2-pyridinyl-2-H-1,2-benzothiazine-2-carboxamide-1,1-dioxide 4-Hydroxy-2-methyl-N-2-pyridinyl-2-H-1,2-benzothiazine-2-carboxamide-1,1-dioxide (10.0 g, 30 mmol) was dissolved in anhydrous methylene chloride and cooled to 0 C. Nitrosonium tetrafluoroborate (4.407 g, 38 mmol) was added in one portion, followed by pyridine (2.98 g, 38 mmol). The reaction mixture was stirred at room temperature for 7 days and then additional nitrosonium tetrafluoroborate (0.571 g, 1.72 mmol) was added. After stirring for 14 days at room temperature, the reaction mixture was poured into saturated sodium bicarbonate solution and extracted with methylene chloride. The solvent was evaporated, the residue was treated with ethyl acetate and filtered. The precipitate was dissolved in the mixture of methylene chloride/ethylacetate (1:1), and the solution was treated with decolorising charcoal, filtered and concentrated in vacuo to give the title compound as a solid (1.56 g, 14%). $^1$H NMR (CDCl$_3$, 300 MHz), δ: 2.96 (s, 3 H), 6.84 (t, 1 H), 7.17 (t, 1 H), 7.60–7.86 (m, 5 H), 8.22 (d, 1 H).

EXAMPLE 16

4-O-Nitroso-hydroxymethylene-(1-(3-benzoyl-α-methylbenzeneacetic acid)) benzyl ester 16a. 3-benzoyl-α-methylbenzeneacetic acid chloride 3-Benzoyl-α-methylbenzeneacetic acid (3.2 g, 12.6 mmol) was treated in the same manner as set forth in Example 13a. Evaporation of the solvent, affored the product as a yellow oil in a quantitative yield. $^1$H NMR (CDCl$_3$), δ: 1.64 (d, 3 H), 4.21 (q, 1 H), 7.45–7.51 (m, 4 H), 7.62 (d, 1 H), 7.72–7.82 (m, 4 H).

16b. 4-Hydroxymethylene-(1-(3-benzoyl-α-methylbenzeneacetic acid)) benzyl ester

Under a nitrogen atmosphere, 1,4-benzenedimethanol (0.507 g, 3.67 mmol) and pyridine (0.145 g, 1.83 mmol) were combined in methylene chloride (5 mL). The resulting solution was stirred for 5 minutes and then cooled to 0° C. A solution of the product of Example 16a (0.500 g, 1.83 mmol) in methylene chloride (5 mL) was added dropwise over 15 minutes. The reaction mixture was allowed to warm to room temperature and was then stirred over 2 days period. The solvent was evaporated and the residue was dissolved in ethyl acetate, washed with 1N hydrochloric acid and saturated sodium bicarbonate solution. The organic phase was dried over anhydrous sodium sulfate and concentrated in vacuo. The residue was purified by flash chromatography on silica-gel eluting with hexane/ethyl acetate (5:1 to 2:1) to give 0.092 g (42%) of the product. $^1$H NMR (CDCl$_3$) δ: 1.60 (d, 3 H), 2.19 (s, 1 H), 3.90 (q, 1 H), 4.71 (s, 2 H), 5.17 (s, 2 H), 7.32 (dd, 4 H), 7.45–7u.82 (m, 7 H), 7.84 (d, 2 H).

16c. 4-O-Nitroso-hydroxymethylene-(1-(3-benzoyl-α-methylbenzeneacetic acid)) benzyl ester The product of Example 16b (0.090 g, 0.24 mmol) was treated in the same manner as set forth in Example 7c. Purification of the crude product was accomplished using flash chromatography on silica gel eluted with hexane/ethyl acetate (1:2) to give 0.069 g (71%) of the title compound as a yellow oil. $^1$H NMR (CDCl$_3$, 300 MHz), δ: 1.55 (3 H), 3.85 (q, 1 H), 5.11 (s, 2 H), 5.67 (s, 2 H), 7.27–7.80 (m, 9 H).

EXAMPLE 17

3-O-Nitroso-hydroxymethylene-(1-(3benzoyl-α-methylbenzeneacetic acid)) benzyl ester 17a. 3-Hydroxymethylene-(1-(3-benzoyl-α-methylbenzeneacetic acid)) benzyl ester Under a nitrogen atmosphere, 1,3-benzenedimethanol (0.500 g, 3.62 mmol) and pyridine (0.193 g, 2.44 mmol) were combined in methylene chloride (7 mL). The resulting solution was stirred for 5 minutes and then cooled to 0 C. A solution of the product of Example 16a (0.665 g, 2.44 mmol) in methylene chloride (5 mL) was added dropwise over 15 minutes. The reaction mixture was stirred 2 h 30 min at 0° C., concentrated in vacuo, diluted with ethyl acetate, washed with 1N hydrochloric acid and saturated sodium bicarbonate solution. The organic phase was dried over anhydrous sodium sulfate and concentrated in vacuo. The residue was purified by flash chromatography on silica gel eluting with hexane/ethyl acetate (2:1) to give 0.530 g (58%) of the product. $^1$H NMR (CDCl$_3$) δ: 1.55 (δ: 3 H), 3.85 (q, 1 H), 4.64 (s, 2 H), 5.12 (d, 2 H), 7.13–7.18 (m, 1 H), 7.22 (s, 1 H), 7.26–7.30 (m, 2 H), 7.40–7.67 (m, 6 H), 7.73–7.78 (m, 3 H).

17b. 3-O-Nitroso-hydroxymethylene-(1-(3-benzoyl-α-methylbenzeneacetic acid)) benzyl ester The product of Example 17a (0.74 g, 0.198 mmol) was treated in the same manner as set forth in Example 7c. Purification of the crude product was accomplished using flash chromatography on silica gel eluted with hexane/ethyl acetate (2:1) to give 0.046 g (71%) of the title compound. $^1$H NMR (CDCl$_3$) δ: 1.55 (d, 3 H), 3.85 (q, 1 H), 5.12 (s, 2 H), 5.65 (s, 2 H), 7.18–7.31 (m, 4 H), 7.40–7.75 (m, 6 H), 7.76–7.79 (m, 3 H).

EXAMPLE 18

3O-Nitroso-hydroxymethylene-1-(1-(3benzoyl-α-methylbenzeneacetic acid))-hydroxymethyladamantyl ester 18a. 1,3-Dicarboxymethyl adamantane 1,3-adamantanedicarboxylic acid (1.5 g, 5.95 mmol) was dissolved in methanol (30 mL) and concentrated sulfuric acid (0.5 mL, 8.90 mmol) was added. The reaction mixture was stirred at room temperature for 20 hours. After concentration in vacuo, the residue was dissolved in methylene chloride, washed with water/brine (1:1), and dried over anhydrous sodium sulfate. The solvent was evaporated to give the product as a white solid in a quantitative yield. $^1$H NMR (CDCl$_3$) δ: 1.65–1.71 (m, 2 H), 1.76–1.82 (m, 8 H), 1.98–2.03 (m, 2 H), 2.07–2.18 (m, 2 H), 3.66 (s, 6 H).

18b. 1,3-Dihydroxymethyl adamantane

Under a nitrogen atmosphere, the product of Example 18a (1.33 g, 5.95 mmol) was dissolved in tetrahydrofuran (20 mL) and lithium aluminum hydride (0.316 g, 8.33 mmol) was added in one portion. The reaction mixture was allowed to reflux for 30 minutes, and was then quenched with water (0.316 mL, 8.33 mmol), 15% sodium hydroxide solution (0.316 mL), and water (0.95 mL). After 15 hours of stirring at room temperature, the reaction mixture was filtered through PTFE and filtrate was partitioned between ethyl acetate and brine. The organic phase was dried over anhydrous sodium sulfate, filtered through PTFE and concentrated in vacuo to give the product (0.370 g, 28%) as a white solid. $^1$H NMR (CDCl$_3$) δ: 1.24–1.29 (m, 2 H), 1.42–1.52 (m, 8 H), 1.61–1.68 (m, 2 H), 2.07–2.16 (m, 2 H), 3.25 (s, 4 H).

18c. 3-Hydroxymethylene-1-(1-(3-benzoyl-α-methylbenzeneacetic acid))-hydroxymethyladamantyl ester The product of Example 18b (0.199 g,0.54 mmol) was dissolved in tetrahydrofuran (10 mL) and pyridine (0.047 g, 0.59 mmol) was added. A solution of the product of Example 16a (0.161 g, 0.59 mmol) in chloroform (3 mL) was added dropwise. The reaction mixture was stirred at room temperature for 40 hours. The solvent was evaporated, the residue was dissolved in methylene chloride, washed with 1N hydrochloric acid, saturated sodium bicarbonate solution and brine, and dried over anhydrous sodium sulfate. The solvent was evaporated and the residue was purified by flash chromatography on silica gel eluted with hexane/ethyl acetate (2:1) to give the product (0.102 g, 28%) as a colorless oil. $^1$H NMR (CDCl$_3$) δ: 1.13–1.17 (m, 2 H), 1.18–1.55 (m, 10 H), 1.98–2.02 (m, 2 H), 3.18 (s, 2 H), 3.66 (d, 2 H), 3.77 (d, 1 H), 3.83 (q, 2 H), 7.43–7.68 (m, 6 H), 7.76–7.81 (m, 3 H).

18d. 3-O-Nitroso-hydroxymethylene-1-(1-(3-benzoyl-α-methylbenzeneacetic acid))-hydroxymethyladamantyl ester The product of Example 18c (0.056 g, 0.083 mmol) was dissolved in anhydrous methylene chloride (2 mL) and pyridine (2 drops) was added. The resulting solution was cooled to −78° C. and nitrosonium tetrafluoroborate was added in one portion. The reaction mixture was stirred for 3 hours at −78° C., washed with water, brine, dried over anhydrous sodium sulfate and concentrated in vacuo. The residue was purified by chromatography on silica gel eluted with hexane/ethyl acetate (15:1) to give the title compound as a colorless oil. $^1$H NMR (CDCl$_3$) δ: 1.15–1.19 (m, 2 H), 1.29–1.61 (m, 10 H), 1.98–2.03 (m, 2 H), 3.65 (d, 1 H), 3.77 (d, 1 H), 3.82 (q, 1 H), 4.33 (s, 2 H), 7.43–7.68 (m, 6 H), 7.76–7.81 (m, 3 H).

EXAMPLE 19

Comparative In Vivo Analgesic, Antiinflammatory and Gastric Lesion Activities

The phenylbenzoquinone-induced writhing test in mice was used to measure analgesic activity. The ability of the compounds to inhibit phenylbenzoquinone-induced writhing in mice was measured using the method of Siegmund et al., *Proc. Soc. Exp. Biol. Med* 95: 729–731, 1957. Male CD-1 mice (Charles River Laboratories, Wilmington, Mass.) weighing 20–25 g were fasted overnight. Vehicle or compounds were administered by oral gavage 1 hour prior to i.p. injection of 2 mg/kg of phenylbenzoquinone. In the case of a nitric oxide adduct being given in combination with a NSAID, the nitric oxide adduct was administered immediately before the NSAID. Five minutes after the i.p. injection of phenylbenzoquinone, the number of writhes in a 5 minute period was counted.

The rat paw edema test was used to measure antiinflammatory activity. The rat paw edema test was performed according to the method of Winter et al., *Proc. Soc. Exp. Biol. Med* 111: 544–547, 1962. Male Sprague-Dawley rats (250–275 g) were fasted overnight and dosed by oral gavage with vehicle or suspensions of compound one hour prior to the subplantar injection of 50 μl of 1% suspension of carrageenin. Three hours later, the paw volume was measured and compared with the initial volume measured immediately after carrageenin injection.

The rat gastric lesion test (Kitagawa et al., *J. Pharmacol. Exp. Ther.*, 253:1133–1137, 1990; Al-Ghamdi et al., *J. Int. Med. Res.*, 19: 2242, 1991) was used to evaluate the potential of compounds to produce gastric lesion. Male Sprague Dawley rats (Charles River Laboratories, Wilmington, Mass.) weighing 230–250 g were used for the experiments. The rats were housed with laboratory chow and water ad libitum prior to the study. The rats were fasted for 24–30 hours with free access to water and then dosed by oral gavage with vehicle or with drugs given at a volume of 0.5 mL/100 g. For the unmodified NSAIDs being given in combination with a nitric oxide adduct (NO-adduct), the NO-adduct was administered by oral gavage immediately prior to the administration of NSAID by oral gavage. Food was withheld for 18 hours after the inital dosing. For acute studies, rats were euthanized by $CO_2$ eighteen hours after dosing and the stomachs were dissected. For the multiple dosing studies, the results of which are in Table 3, food was given eighteen hours after the first dose and the rats were maintained on food and water ad libitum while receiving a single daily dose for the remainder of the experiment. For the multiple dosing studies, the results of which are in Table 4, the rats were either fasted 24–30 hours before the first dosing and for 4 hours after the first dosing, (4 day study with ketoprofen, Example 4, and Example 6); allowed access to food and water ad libitum before as well as during the experiment, (7 day study with ketoprofen and Example 4); or fasted 24–30 hours prior to the first dosing and for 18 hours after the first dosing, (7 day study with ibuprofen, Example 11, and Example 12). The stomachs were dissected along the greater curvature, washed with a directed stream of 0.9% saline and pinned open on a sylgard based petridish for examination of the hemorrhagic lesion. Gastric lesion score was expressed in mm and calculated by summing the length of each lesion.

Table 1 shows the relative activities of compounds in the analgesic, antiinflammatory and gastric lesion tests, and are expressed, for each novel NSAID compound, as described according to the general formulas (I), (II), (III) and (IV), or NSAID coadministered with an NO-adduct, as the ratio of activity relative to the parent NSAID.

TABLE 1

| Compound | Relative Activity | | |
|---|---|---|---|
|  | Analgesia | Antiinflammation | Gastric Lesion |
| Ketoprofen | 1 | 1 | 1 |
| Example 4 | 1.6 | 0.58 | 0.03 |
| Example 6 | 1 | ND | ND |
| Example 5 | 1.1 | ND | ND |
| Example 16 | 1.1 | ND | ND |
| Flurbiprofen | 1 | 1 | 1 |
| Example 13 | 0.31 | 1.83 | 0.5 |
| Indomethacin | 1 | 1 | 1 |
| Example 8 | 1 | 1 | 0.08 |
| Ibuprofen | ND | 1 | 1 |
| Example 12 | ND | 1 | <0.03 |
| Example 11 | ND | 1 | <0.05 |
| Piroxicam | 1 | ND | 1 |
| Piroxicam + Example 2 | 2.3 | ND | 0.08 |

ND — not determined

Table 2 shows the results of single dose treatment studies in which various NO-adducts were administered in combination with various NSAIDs. The combinations are able to protect against the NSAID induced gastric toxicity.

TABLE 2

| NSAID | (mg/kg) | NO-Adduct | Molar Dose Ratio NSMD:NO-Adduct | Gastric Lesion Protection |
|---|---|---|---|---|
| Piroxicam | 16 | Example 2 | 1:1 | +++ |
| Piroxicam | 8 | Example 2 | 1:1 | +++ |
| Piroxicam | 8 | Isoamyl nitrite | 1:3 | +++ |
| Piroxicam | 8 | Isosorbide dinitrate | 1:3 | +++ |
| Piroxicam | 8 | Example 1 | 1:2 | ++ |
| Flurbiprofen | 16 | Example 2 | 1:1 | ++ |
| Tenidap | 16 | Example 2 | 1:1 | ++ |

TABLE 2-continued

| NSAID | (mg/kg) | NO-Adduct | Molar Dose Ratio NSMD:NO-Adduct | Gastric Lesion Protection |
|---|---|---|---|---|

70–100% Protection = +++; 40–69% Protection = ++; 20–39% Protection = +

Table 3 shows the results of multiple dose treatment studies in which various NO-adducts were administered in combination with various NSAIDs. The combinations are able to protect against the NSAID induced gastric toxicity.

TABLE 3

| Treatment (Days) | NSAID | (mg/kg) | NO-Donor | Mole Dose Ratio NSAID:NO-Adduct | Gastric Lesion Protection |
|---|---|---|---|---|---|
| 3 | Piroxicam | 16 | Example 2 | 1:1 | +++ |
| 14 | Piroxicam | 16 | Example 2 | 1:1 | ++ |
| 7 | Ibuprofen | 40 | Example 2 | 1:1 | + |
| 14 | Ibuprofen | 30 | Example 2 | 1:1 | ++ |

70–100% Protection = +++; 40–69% Protection = ++; 20–39% Protection = +

Table 4 shows the results of multiple dose treatment studies in which various novel NSAID compounds directly or indirectly linked to various NO-adducts were administered. The modified NSAIDs containing NO-adducts produced significantly less gastric toxcity.

TABLE 4

| Compound | (mg/kg) | Treatment (Days) | Relative Gastric Lesion Activity |
|---|---|---|---|
| Ketoprofen | 10 | 4 | +++++ |
| Example 4 | 14 | 4 | + |
| Example 6 | 15 | 4 | ++ |
| Ketoprofen | 10 | 7 | +++++ |
| Example 4 | 14 | 7 | + |
| Ibuprofen | 30 | 7 | +++++ |
| Example 11 | 50 | 7 | + |
| Example 12 | 45 | 7 | + |
| Vehicle | | 7 | + |

100% of the gastric toxcity induced by the parent NSAID = +++++
21–40% of the gastric toxcity induced by the parent NSAID = ++
1–20% of the gastric toxcity induced by the parent NSAID = +

What is claimed is:

1. A composition comprising a nonsteroidal antiinflammatory drug wherein the nonsteroidal antiinflammatory drug is a salicylic acid, a fenamate, or a pharmaceutically acceptable salt thereof, and a compound that donates, transfers or releases nitric oxide, elevates endogenous levels of nitric oxide, or is a substrate for nitric oxide synthase.

2. The composition of claim 1, wherein the salicylic acid or the fenamate is a compound of formula IV or a pharmaceutically acceptable salt thereof:

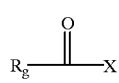

IV wherein X is —OH; and $R_g$ is:

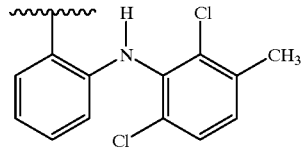

(1)

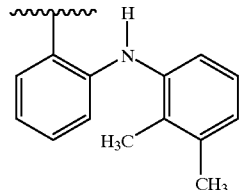

(2)

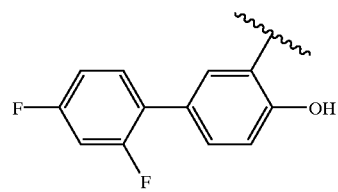

(3)

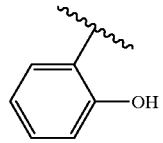

(4)

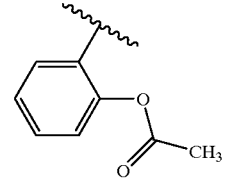

(5)

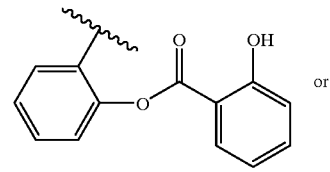

(6)

or

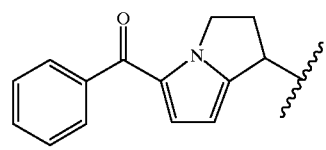

(7)

3. The composition of claim 1, wherein the salicylic acid is acetylsalicylic acid, diflunisal, salsalate, sodium salicylate, salicylamide, sodium thiosalicylate, choline salicylate, magnesium salicylate, mesalamine, sulfasalazine, methylsalicylate, or a pharmaceutically acceptable salt thereof.

4. The composition of claim 1, wherein the fenamate is mefenamic, meclofenamic, flufenamic, tolfenamic, etofenamic acid or a pharmaceutically acceptable salt thereof.

5. The composition of claim 1, wherein the compound that donates, transfers or releases nitric oxide, elevates endogenous synthesis levels of nitric oxide, or is a substrate for nitric oxide synthase is L-arginine.

6. The composition of claim 1, wherein the compound that donates, transfers or releases nitric oxide, elevates endogenous synthesis levels of nitric oxide, or is a substrate for nitric oxide synthase is an S-nitrosothiol.

7. The composition of claim 6, wherein the S-nitrosothiol is S-nitroso-N-acetylcysteine, S-nitroso-N-acetylpenicillamine, S-nitroso-homocysteine, S-nitroso-cysteine or S-nitroso-glutathione.

8. The composition of claim 6, wherein the S-nitrosothiol is:

(i) $CH_3(C(R_b)(R_c))_xSNO$;

(ii) $HS(C(R_b)(R_c))_xSNO$; or (iii) $ONS(C(R_b)(R_c))_xQ$;

wherein x is 2 to 20; $R_b$ and $R_c$ are each independently a hydrogen atom, a lower alkyl group, a cycloalkyl group, an aryl group, a heteroaryl group, an arylalkyl group, an alkylamino group or a dialkylamino group, or $R_b$ and $R_c$ taken together are a cycloalkyl group or a bridged cycloalkyl group; and Q is fluoro, alkoxy, cyano, carboxamido, cycloalkyl, arylalkoxy, alkylsulfinyl, arylthio, alkylamino, dialkylamino, hydroxy, carbamoyl, N-alkylcarbamoyl, N,N-dialkylcarbamoyl, amino, carboxyl, hydrogen, nitro or aryl.

9. The composition of claim 1, wherein the compound that donates, transfers or releases nitric oxide, elevates endogenous synthesis levels of nitric oxide, or is a substrate for nitric oxide synthase is:

(i) a compound that comprises at least one ON—O— group, ON—N— group or ON—C— group, wherein the compound that comprises at least one ON—O— group, ON—N— group or ON—C— group is an ON—O-polypeptide, an ON—N—polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, an ON—O-heterocyclic compound, an ON—N-heterocyclic compound, an ON—C-heterocyclic compound, an ON—O— straight or branched, saturated or unsaturated, substituted or unsubstituted aliphatic or aromatic hydrocarbon, an ON—N— straight or branched, saturated or unsaturated, substituted or unsubstituted aliphatic or aromatic hydrocarbon, or an ON—C— straight or branched, saturated or unsaturated, substituted or unsubstituted aliphatic or aromatic hydrocarbon;

(ii) an N—oxo—N-nitrosoamine having the formula $R_1R_2$—N(O—M$^+$)—NO, wherein $R_1$ and $R_2$ are each independently a polypeptide, an amino acid, a sugar, an oligonucleotide, a straight or branched, saturated or unsaturated, aliphatic or aromatic, substituted or unsubstituted hydrocarbon group, or a heterocyclic group; and M$^+$ is a metal cation; or (iii) a thionitrate having the structure R—(S)$_v$—NO, wherein v is an integer of at least 2, and R is a polypeptide, an amino acid, a sugar, an oligonucleotide, or a straight or branched, saturated or unsaturated, aliphatic or aromatic hydrocarbon.

10. The composition of claim 1, wherein the compound that donates, transfers or releases nitric oxide, elevates endogenous synthesis levels of nitric oxide, or is a substrate for nitric oxide synthase is a compound comprising at least one —SNO group, wherein the compound comprising at least one —SNO group is an S-nitroso-polypeptide, an S-nitrosylated amino acid, an S-nitrosated sugar, an S-nitrosated oligonucleotide, a heterocyclic compound having at least one —SNO group, or a straight or branched, saturated or unsaturated, substituted or unsubstituted, aliphatic or aromatic S-nitroso hydrocarbon.

11. A method for treating inflammation, pain, gastrointestinal lesions or fever in an animal in need thereof comprising administering the composition of claim 1 to the animal to treat the inflammation, pain, gastrointestinal lesion or fever.

12. A method of reducing the gastrointestinal toxicity or renal toxicity of a nonsteroidal antiinflammatory drug administered to an animal comprising administering the composition of claim 1 to the animal to reduce the gastrointestinal toxicity or renal toxicity of the nonsteroidal antiinflammatory drug.

13. A composition comprising a nonsteroidal antiinflammatory drug, wherein the nonsteroidal antiinflammatory drug is acetylsalicylic acid, diflunisal, salsalate, sodium salicylate, salicylamide, sodium thiosalicylate, choline salicylate, magnesium salicylate, mesalamine, sulfasalazine, methylsalicylate, mefenamic, meclofenamic, flufenamic, tolfenamic, etofenamic acid, or pharmaceutically acceptable salts thereof, and a compound that donates, transfers or releases nitric oxide, elevates endogenous levels of nitric oxide, or is a substrate for nitric oxide synthase.

14. A method for treating inflammation, pain, gastrointestinal lesions or fever in an animal in need thereof comprising administering the composition of claim 13 to the animal to treat the inflammation, pain, gastrointestinal lesion or fever.

15. A method of reducing the gastrointestinal toxicity or renal toxicity of a nonsteroidal antiinflammatory drug administered to an animal comprising administering the composition of claim 13 to the animal to reduce the gastrointestinal toxicity or renal toxicity of the nonsteroidal antiinflammatory drug.

16. A method for accelerating gastrointestinal tissue repair in an animal in need thereof comprising administering to the animal a therapeutically effective amount of the composition of claim 1.

17. A method for treating inflammatory bowel disease in an animal in need thereof comprising administering to the animal a therapeutically effective amount of the composition of claim 1.

18. A method for treating an inflammatory disease state or disorder in an animal in need thereof comprising administering to the animal a therapeutically effective amount of the composition of claim 1.

19. The method of claim 18, wherein the inflammatory disease state or disorder is a reperfusion injury to an ischemic organ, a myocardial infarction, inflammatory bowel disease, rheumatoid arthritis, osteoarthritis, hypertension, psoriasis, an organ transplant rejection, organ preservation, impotence, a radiation-induced injury, asthma, atherosclerosis, thrombosis, platelet aggregation, metastasis, influenza, a stroke, a burn, a trauma, acute pancreatitis, pyelonephritis, hepatitis, an autoimmune disease, insulin-dependent diabetes mellitus, disseminated intravascular coagulation, a fatty embolism, Alzheimer's disease, an adult respiratory disease, an infantile respiratory disease, carcinogenesis, or a hemorrhage in a neonate.

20. The method of claim 19, wherein the inflammatory disease state or disorder is inflammatory bowel disease.

21. A method for accelerating gastrointestinal tissue repair in an animal in need thereof comprising administering to the animal a therapeutically effective amount of the composition of claim 13.

22. A method for treating inflammatory bowel disease in an animal in need thereof comprising administering to the animal a therapeutically effective amount of the composition of claim 13.

23. A method for treating an inflammatory disease state or disorder in an animal in need thereof comprising administering to the animal a therapeutically effective amount of the composition of claim 13.

24. The method of claim 23, wherein the inflammatory disease state or disorder is a reperfusion injury to an ischemic organ, a myocardial infarction, inflammatory bowel disease, rheumatoid arthritis, osteoarthritis, hypertension, psoriasis, an organ transplant rejection, organ preservation, impotence, a radiation-induced injury, asthma, atherosclerosis, thrombosis, platelet aggregation, metastasis, influenza, a stroke, a burn, a trauma, acute pancreatitis, pyelonephritis, hepatitis, an autoimmune disease, insulin-dependent diabetes mellitus, disseminated intravascular coagulation, a fatty embolism, Alzheimer's disease, an adult respiratory disease, an infantile respiratory disease, carcinogenesis, or a hemorrhage in a neonate.

25. The method of claim 24, wherein the inflammatory disease state or disorder is inflammatory bowel disease.

26. The composition of claim 1, further comprising a pharmaceutically acceptable carrier.

27. The composition of claim 13, further comprising a pharmaceutically acceptable carrier.

28. A kit comprising the composition of claim 1.

29. A kit comprising the composition of claim 13.

30. A kit comprising a salicylic acid, a fenamate, or a pharmaceutically acceptable salt thereof, and a compound that donates, transfers or releases nitric oxide, elevates endogenous levels of nitric oxide, or is a substrate for nitric oxide synthase.

31. The kit of claim 30, wherein the salicylic acid, the fenamate, or the pharmaceutically acceptable salt thereof, and the compound that donates, transfers or releases nitric oxide, elevates endogenous levels of nitric oxide, or is a substrate for nitric oxide synthase are separate components in the kit or are in the form of a composition in the kit.

* * * * *

UNITED STATES PATENT AND TRADEMARK OFFICE
CERTIFICATE OF CORRECTION

PATENT NO. : 6,043,233
DATED : March 28, 2000
INVENTOR(S) : David S. Garvey, et al.

Page 1 of 1

It is certified that error appears in the above-identified patent and that said Letters Patent is hereby corrected as shown below:

Title Page [62] Related U.S. Application Data, after "08/931,564, Sep. 16, 1997" insert --now U.S. Patent No. 6,057,347--, and "08/425,090, Apr. 19, 1995, abandoned " should read --08/425,090, April 19,1995, now U.S. Patent No. 6,051,588.

Col. 1, line 6, after "Sep. 16, 1977", insert -- now U.S. Patent No. 6,057,347--and line 10, delete "now abandoned' and insert --now U.S. Patent No.6,051,588.

Col. 2, line 2, delete "antuinflammatory" and insert--antiinflammatory--;
line 5, delete "antdnflammatory" and insert --antiinflammatory.
Col. 24, line 24, delete "an" and insert --in--.
Col. 26, line 13, delete "vacumm" and insert --vacuum--.
Col. 41, line 42, after "unsubstituted" insert--,--;
line 44, after "unsubstituted" insert --,--;
line 47, after "unsbustituted "insert--,--.

Signed and Sealed this

Fifth Day of June, 2001

*Attest:*

*Attesting Officer*

NICHOLAS P. GODICI
*Acting Director of the United States Patent and Trademark Office*